(12) United States Patent
Wilson et al.

(10) Patent No.: US 11,723,838 B2
(45) Date of Patent: Aug. 15, 2023

(54) PRESERVATIVE REMOVAL FROM EYE DROPS

(71) Applicant: TearClear Corp., Copley, OH (US)

(72) Inventors: Michael Wilson, Middleburg, FL (US); Michael Williams, Keystone Heights, FL (US); Deniz Hay, Gainesville, FL (US); Michael Malanga, Midland, MI (US)

(73) Assignee: TearClear Corp., Copley, OH (US)

( * ) Notice: Subject to any disclaimer, the term of this patent is extended or adjusted under 35 U.S.C. 154(b) by 518 days.

(21) Appl. No.: 16/862,918

(22) Filed: Apr. 30, 2020

(65) Prior Publication Data

US 2020/0346186 A1 Nov. 5, 2020

Related U.S. Application Data

(60) Provisional application No. 62/842,071, filed on May 2, 2019.

(51) Int. Cl.
| | |
|---|---|
| *A61J 1/14* | (2023.01) |
| *A61K 31/382* | (2006.01) |
| *A61K 31/4985* | (2006.01) |
| *A61K 31/517* | (2006.01) |
| *A61K 31/5377* | (2006.01) |

(Continued)

(52) U.S. Cl.
CPC ........ *A61J 1/1456* (2015.05); *A61J 1/1468* (2015.05); *A61K 31/382* (2013.01); *A61K 31/4985* (2013.01); *A61K 31/517* (2013.01); *A61K 31/5377* (2013.01); *A61K 31/5383* (2013.01); *B01D 71/26* (2013.01); *B01J 20/265* (2013.01); *B01J 20/28004* (2013.01); *B01J 20/28016* (2013.01); *B01J 20/28042* (2013.01);

(Continued)

(58) Field of Classification Search
None
See application file for complete search history.

(56) References Cited

U.S. PATENT DOCUMENTS

| | | |
|---|---|---|
| 3,293,112 A | 12/1966 | Kehr |
| 3,322,711 A | 5/1967 | Bush et al. |

(Continued)

FOREIGN PATENT DOCUMENTS

| | | |
|---|---|---|
| CN | 101291636 A | 10/2008 |
| CN | 114096339 A | 2/2022 |

(Continued)

OTHER PUBLICATIONS

PCT/US2020/030801 International Preliminary Report on Patentability dated Nov. 2, 2021.

(Continued)

*Primary Examiner* — Clare M Perrin
(74) *Attorney, Agent, or Firm* — Wilson Sonsini Goodrich & Rosati

(57) ABSTRACT

A particulate plug for removing a preservative from a solution, suspension, or emulsion comprising a drug is presented. The plug comprises microparticles of oxidized polyolefin (OxPO). The microparticles are irregular-shaped rigid aggregates and are sized and packed to yield a hydraulic permeability greater than 0.01 Da. The OxPO have absorbed portions of a preservative to be removed and/or a drug for delivery in solution, as can the copolymer.

23 Claims, 2 Drawing Sheets

(51) Int. Cl.
*A61K 31/5383* (2006.01)
*B01D 71/26* (2006.01)
*B01J 20/28* (2006.01)
*B01J 20/26* (2006.01)
*A61F 9/00* (2006.01)

(52) U.S. Cl.
CPC ......... *A61F 9/0008* (2013.01); *B01J 2220/52* (2013.01); *B01J 2220/56* (2013.01)

(56) References Cited

U.S. PATENT DOCUMENTS

| | | | |
|---|---|---|---|
| 4,459,388 | A | 7/1984 | Hettche et al. |
| 5,013,459 | A | 5/1991 | Gettings et al. |
| 5,056,689 | A | 10/1991 | Heyl et al. |
| 5,064,908 | A | 11/1991 | Schuster et al. |
| 5,080,800 | A | 1/1992 | Heyl et al. |
| 5,401,811 | A | 3/1995 | Stuart, Jr. |
| 5,863,562 | A | 1/1999 | Tsao et al. |
| 7,622,031 | B2 | 11/2009 | Seven et al. |
| 10,123,904 | B2 | 11/2018 | Chauhan et al. |
| 11,096,865 | B2 | 8/2021 | Wilson et al. |
| 2010/0285192 | A1 * | 11/2010 | Daoust ................. C12H 1/0424 426/422 |
| 2010/0305259 | A1 | 12/2010 | Rodriguez et al. |
| 2013/0127071 | A1 | 5/2013 | Sugimoto et al. |
| 2015/0150719 | A1 | 6/2015 | Chibret et al. |
| 2017/0224531 | A1 | 8/2017 | Chauhan et al. |
| 2020/0246222 | A1 | 8/2020 | Malanga et al. |

FOREIGN PATENT DOCUMENTS

| | | |
|---|---|---|
| EP | 2531154 A1 | 12/2012 |
| GB | 1087915 A | 10/1967 |
| WO | WO-2005066219 A1 | 7/2005 |
| WO | WO-2007045913 A2 | 4/2007 |
| WO | WO-2011095877 A1 | 8/2011 |
| WO | WO-2016085885 A1 | 6/2016 |
| WO | WO-2018102817 A1 | 6/2018 |
| WO | WO-2019060846 A1 * | 3/2019 ........... A61F 9/0008 |
| WO | WO-2019195734 A1 | 10/2019 |
| WO | WO-2020223527 A2 | 11/2020 |
| WO | WO-2022031841 A1 | 2/2022 |

OTHER PUBLICATIONS

Clariant International Ltd. Licolub(R) H 12 fine grain. Oxidized, high density polyethylene max. (2014).
Deurez, The Wax Company. Polyethylene waxes, technical data (2020).
PCT/US2020/030801 International Search Report and Written Opinion dated Aug. 4, 2020.
Dec. 9, 2021 Restriction Requirement U.S. Appl. No. 17/394,023.
Feb. 24, 2022 Non-Final Office Action U.S. Appl. No. 17/394,023.
International Search Report and Written Opinion dated Jan. 19, 2022 for International Application No. PCT/US2021/445334.
U.S. Appl. No. 16/932,623 First Action Interview dated Jan. 4, 2021.
Anonymous: Flame Treatment—an overview, Science Direct Topics, 2014, pp. 1-15, retrieved from the Internet: URL: https://www.sciencedirect.com/topics/engineering/flame-treatment [retrieved on Oct. 20, 2022].
European Patent Application No. 20798350.3 Extended European Search Report dated Oct. 28, 2022.
Chinese Application No. 202080048648X First Office Action dated Feb. 16, 2023.

* cited by examiner

PRESERVATIVE REMOVAL FROM EYE DROPS

CROSS REFERENCE TO RELATED APPLICATIONS

This application claims the benefit of U.S. Provisional Application No. 62/842,071 filed May 2, 2019, which is incorporated by reference in the disclosure of this application.

BACKGROUND

Ophthalmic diseases are commonly treated with prescribed multi-dose medications packaged in eye drop bottles due to ease of use, availability, affordability, and patient compliance. The frequency of topical eye drop application varies from one or two times a day for diseases like glaucoma to as many as ten times a day for severe infections. Although eye drops formulations are packed under sterile conditions, the potential risk of contamination after prolonged use or improper handling can be a key factor contributing to ocular infections. In some cases, as a frugal measure, multiple patients tend to use the same multi-dose containers to administer medications, overlooking the possibility of ocular infections due to cross-contamination, particularly if the protocol for disinfecting the nozzle is not followed. Most ophthalmic formulations now contain an added preservative to maintain the shelf life of the sterile medication and eliminate microbial growth. The US Food and Drug Administration has imposed regulations on multi-dose ophthalmic formulations, mandating the addition of preservatives to provide microbe-free medication. A variety of preservatives are used to serve this purpose. Preservatives are needed for maintaining sterility, but the benefit is often offset by adverse side effects of the preservatives, even among healthy subjects.

Benzalkonium chloride (BAK), a quaternary ammonium compound with high efficacy, is used prominently. BAK is an active detergent disinfecting agent, which interrupts the lipid membranes of cells, thereby inhibiting the growth of microorganisms. Despite an acceptable tolerance and safety profile of BAK, many studies have shown commercial topical medications with added BAK content induce severe toxic side effects. Well-documented adverse effects of BAK include tear film instability, trabecular and corneal cells growth retardation and corneal and conjunctival inflammation. Cytotoxicity studies show that BAK disrupts ocular surface cells and tissues, whose impact in glaucoma and dry eye patients requiring long-term and frequent dosing is deleterious. Corneal endothelial damage occurs upon prolonged use of topical medication with added benzalkonium chloride. High tear film instability and disruption of the corneal barrier is observed using the preserved glaucoma drug Timolol to a greater extent than when using preservative-free Timolol in healthy subjects. The detergent action of BAK solution disrupts superficial lipid layers of the tear film into oil droplets solubilized by a single drop of 0.01% BAK solution.

In 2009, the European Medicines Agency's Committee for Medicinal Products for Human Use concluded that unpreserved formulations "are needed for patients with lower tolerance to preservatives," and "for long-term treatment, formulations without preservatives are valuable alternatives." Considering the adverse effects of preservatives, the development of safe eye drop dispensing devices to deliver preservative-free formulations has been pursued for more than a decade. Preservative-free formulations are available in single-dose containers to eliminate the need for preservatives; however, these are not convenient and too expensive for wide public use.

U.S. Pat. No. 5,080,800 teaches a process for removing components from solutions, including preservatives from eye-drops. The process involves the use of ion exchange resins to selectively remove ocular preservatives. Ion exchange resins have not been tested extensively for biocompatibility and cytotoxicity, and inherently are non-selective for molecules of same charge, adsorb ionic drugs as readily as any ionic preservative such as BAK. The hydraulic permeability of these resins is not addressed although this characteristic is critical for devices that allow formation of drops without excessive pressure. U.S. Pat. No. 5,080,800 does not teach on the importance of ensuring that the filters are designed to resist growth of microorganisms that may remain trapped. U.S. Pat. No. 5,080,800 does not teach on the necessary requirements to ensure that the concentration of the active drug in the drops coming out of the device do not fall below the minimum requirements based. Hence a practical way of retaining the beneficial behavior of preservatives while avoiding their toxic effects in the eye remains a need.

SUMMARY

Embodiments of the disclosure are directed to particulate plugs for selectively removing a large fraction of the preservative without significantly removing the drug and specifically directed to achieving this for each eluting drop. The material of the plug may be designed to minimize drug binding. The material of the plug may depend on the properties of the drug whose binding is to be minimized. The binding may depend on the structure of the drug and/or the detailed structure of the matrix materials of the particles of the tip. Broadly, ophthalmic drugs can be divided into hydrophobic and hydrophilic categories depending of the affinity of the drug for water. Hydrophilic drugs are more soluble in water while hydrophobic drugs are less soluble. By combining one or more different monomers into the formulation for making the particles, the material may selectively remove a preservative while minimizing binding of the drug.

Embodiments of the disclosure are directed to particulate plugs for removing a preservative from a drug solution where microparticles comprising the plug are oxidized polyolefins (OxPO). In some embodiments the OxPO is an oxidized polyethylene. In some embodiments the OxPO is an oxidized high density polyethylene (OxHDPE). The microparticles can be round, ovoid, smooth surfaced or irregular-shaped rigid aggregates that form a particulate plug having a hydraulic permeability greater than 0.01 Da and where the plug fits an outlet of a container for a solution, emulsion, or suspension. In some embodiments, the OxPO-comprising plugs further comprise absorbed portions of a preservative to be removed and/or a drug for delivery in solution, wherein the particulate plug rapidly and selectively removes a preservative from the solution, emulsion, or suspension.

The drug can be a hydrophilic drug, for example, Timolol Maleate, Levofloxacin, Dorzolamide, Brimonidine Tartrate, or and/or hydrophobic drugs, for example, latanoprost or bimatoprost, and/or a combination of hydrophilic drugs, for example, brimonidine and timolol (aka Combigan). The preservative may be Benzalkonium chloride (BAK).

Another embodiment of the disclosure is directed to a method of removing a preservative from a drug solution, where a container has an extended outlet and a chamber for holding a drug solution comprising at least one drug and a preservative where the extended outlet is packed with a particulate plug and the drug solution is forced through the particulate plug. The particulate plug can be preloaded with the drug or with the preservative.

In an aspect, the present disclosure provides a particulate plug for removing a preservative from a solution comprising a drug. The plug may comprise microparticles of OxPO, wherein the microparticles are of any shape and form a particulate plug having a hydraulic permeability greater than 0.01 Da and fits an outlet of a container for a solution, emulsion, or suspension, wherein the OxPO optionally further comprises absorbed portions of a preservative to be removed and/or a drug for delivery in solution, wherein the particulate plug rapidly and selectively removes a preservative from the solution, emulsion, or suspension.

In another aspect, the present disclosure provides a method of removing a preservative from a drug solution, suspension, or emulsion. The method may comprise providing a container having an extended outlet and a chamber for holding the drug solution, suspension, or emulsion comprising at least one drug and a preservative; the container comprising a particulate plug comprising OxPO within the extended outlet; and forcing the drug solution, suspension, or emulsion through the particulate plug.

In some embodiments, the method further comprises preloading the particulate plug with the drug and/or with the preservative. In some embodiments, the drug comprises Timolol Maleate, Levofloxacin, Dorzolamide, Brimonidine Tartrate, or a combination thereof, such as brimonidine and timolol (aka Combigan). In some embodiments, the preservative is Benzalkonium chloride (BAK). In some embodiments, the plug comprises OxPO. In some embodiments, the plug comprises an OxPO selected from an OxHDPE.

In another aspect, the present disclosure provides a device for delivery of a pharmaceutical formulation, the device comprising the particulate plug any embodiment and a pharmaceutical formulation comprising one or more active components and a preservative, wherein when the pharmaceutical formulation is forced through the particulate plug at least 90% of the preservative is selectively removed, while at least 90% of the one or more active components are retained in the delivered pharmaceutical formulation.

In some embodiments, the device is an eye drop bottle for dispensing drops of the pharmaceutical formulation and wherein the concentration of the one or more active components in a dispensed drop is at least 90% of that of the formulation inside the eye drop bottle, for every drop of the formulation forced through the plug. In some embodiments, the particulate plug comprises a packed bed of particles. In some embodiments, the device has a holder assembly to retain the particulate plug while forcing the formulation through the plug. In some embodiments, the particulate plug comprises a formulation entry face and a formulation exit face, and the holder assembly comprises filters on the solutions entry and exit faces of the particulate plug. In some embodiments, the holder assembly comprises a solution permeable bag around the particulate plug. In some embodiments, the particulate plug is sintered to fuse the particulate plug as a porous monolith. In some embodiments, the particulate plug has a partition coefficient for the preservative that is at least 100 and a partition coefficient for each active component that is less than 1. In some embodiments, the particulate plug is pre-equilibrated with the drug. In some embodiments, the device further comprises packaging that holds the device in a position for forcing the formulation through the particulate plug from manufacture until the device is received by a patient for use.

In another aspect, the present disclosure provides a preservative removing device. The preservative removing device may comprise microparticles of OxPO, wherein the microparticles are of any shape, wherein the microparticles form a particulate plug having a hydraulic permeability greater than 0.01 Da, wherein the plug fits an outlet of a container for a solution, emulsion, or suspension, wherein the OxPO further comprises absorbed portions of a preservative to be removed and a therapeutic agent for delivery, wherein the particulate plug rapidly and selectively removes a preservative from the solution, emulsion, or suspension.

In another aspect, the present disclosure provides a method of removing a preservative from a drug solution, suspension, or emulsion, according to any embodiment. The method may comprise providing a container having an extended outlet and a chamber for holding the drug solution, suspension, or emulsion, the drug solution, suspension, or emulsion comprising at least one drug and a preservative; wherein the container comprises a particulate plug for removing the preservative from the solution, suspension, or emulsion, the particulate plug within the extended outlet; and forcing the drug solution, suspension, or emulsion through the particulate plug. In some embodiments, the method further comprises preloading the particulate plug with the drug or with the preservative.

In another aspect, the present disclosure provides a device for delivery of a pharmaceutical formulation, comprising the particulate plug of any embodiment and a pharmaceutical formulation comprising one or more active components and a preservative, wherein when the pharmaceutical formulation is forced through the particulate plug at least 90% of the preservative is selectively removed while at least 90% of all active components are retained in the delivered pharmaceutical formulation.

In some embodiments, the device is an eye drop bottle for dispensing drops of the pharmaceutical formulation and wherein the concentration of the active components in a dispensed drop is at least 90% of that of the formulation inside the eye drop bottle for every drop of the solution forced through the plug. In some embodiments, the device has a holder assembly to retain the particulate plug while forcing the solution through the particulate plug. In some embodiments, the particulate plug comprises a formulation entry face and a formulation exit face, and the holder assembly comprises filters on the entry and exit faces of the particulate plug. In some embodiments, the device further comprises packaging that holds the device in a position for forcing the solution, suspension, or emulsion through the particulate plug from manufacture until the device is received by a patient for use.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

The present disclosure provides a preservative removal agent. A preservative removal agent may rapidly and selectively remove preservatives of the present disclosure from a solution, emulsion, or suspension comprising a therapeutic agent. The preservative removal agent may rapidly and selectively extract the preservative, allowing the eye drop formulation to flow through the plug with minimal pressure drop, yet with sufficient time to remove the preservative and with sufficient surface area to adsorb the preservative. The matrix may comprise a material with a high affinity for the preservative, such as for example benzalkonium chloride (BAK), and low affinity for a therapeutic agent, such as a drug or other ophthalmological agent.

Aspects of the present disclosure provide a preservative removal agent which may comprise a porous polymer matrix. In some cases, the preservative removal agent comprises OxPO. In some embodiments, the OxPO is an oxidized high-density polyethylene (OxHDPE).

The present disclosure provides a particulate plug for removing a preservative from a solution comprising a drug. The particulate plug may comprise microparticles of an OxPO. The microparticles may be irregular-shaped rigid aggregates and may form a particulate plug having a hydraulic permeability greater than 0.01 Darcy (Da). The plug may fit an outlet of a container for a solution, emulsion, or suspension. In some cases, the OxPO microparticles further comprise absorbed portions of a preservative to be removed and/or a drug for delivery in solution. The particulate plug may rapidly and selectively remove a preservative from the solution, emulsion, or suspension.

Figure 1:
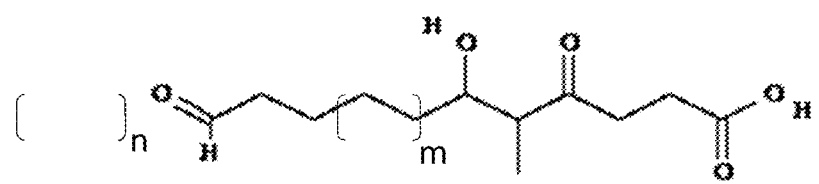
FIG. 1 shows an example structure of Oxidized High Density Polyethylene (OxHDPE), in accordance with some embodiments.

FIG. 1 shows an example structure of OxHDPE, in accordance with some embodiments.

Figure 2:
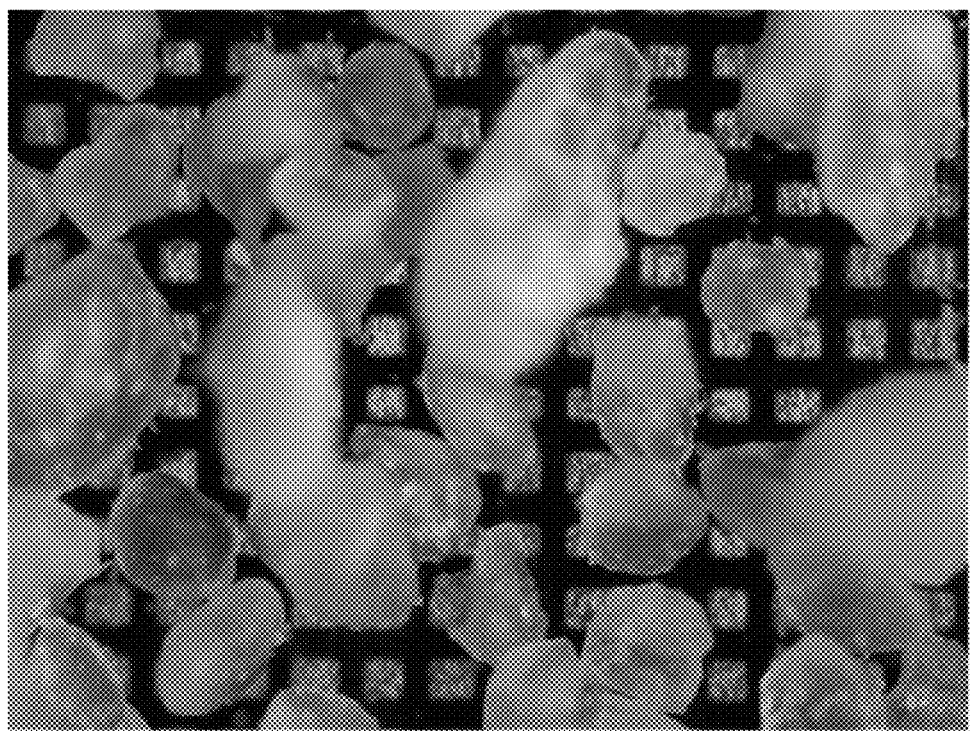
FIG. 2 shows optical images of example Oxidized High Density Polyethylene (OxHDPE) microparticles with 125-250 micron size on a background grid of 100 microns, in accordance with some embodiments.

FIG. 2 shows optical images of example OxHDPE microparticles with 125-250 micron size on a background grid of 100 microns, in accordance with some embodiments.

Preservative Removal Agent

In some embodiments, the disclosure provides pharmaceutical formulations comprising a preservative and a therapeutic agent. The formulation may comprise a solution, emulsion, or suspension of a therapeutic agent and a preservative. In some embodiments, the formulation may comprise a preservative removal agent, (e.g. in embodiments where the preservative removal agent may comprise a portion of a solution, emulsion, or suspension comprising a therapeutic agent and a preservative). In other embodiments, the preservative removal agent may be separate from the solution, emulsion, or suspension comprising the therapeutic agent and the preservative (e.g. in embodiments where the preservative removal agent may be located within the neck of a bottle). Optionally in any embodiment, the solution, emulsion, or suspension may additionally comprise one or more pharmaceutically acceptable excipients.

In some embodiments, a matrix disposed within a nozzle may be a porous polymeric matrix. Applying a pressure behind the nozzle may cause fluid to flow through the nozzle via the flow path, along which path the preservative may be removed by adsorption onto the matrix. The polymer material, the hydraulic permeability, the partition coefficient, the adsorption rate, and the pore size in combination provide for the absorption of all, or most of, the preservative from the solution and thus from the drop administered to the patient eye. The reduced-preservative solution may subsequently be delivered directly to the eye. The porous polymeric matrix may rapidly and selectively extract the preservative, allowing the eye drop formulation to flow through the plug with minimal pressure drop, yet with sufficient time to remove the preservative and with sufficient surface area to adsorb the preservative.

The porous polymeric matrix comprises oxidized polyolefin (OxPO) microparticles. An oxidized polyolefin is prepared by thermal and/or chemical degradation of a high molecular weight polyolefin resin. The oxidation of polyolefins to form oxidized waxes is known in the art. For example, polyethylenes can be oxidized by the action of oxygen at elevated temperatures to obtain oxidized products through chain degradation. (See, e.g., U.S. Pat. Nos. 3,293,112; 3,322,711; 4,459,388; and GB 1,087,915.) In one method, oxidation occurs while the polyethylene is in the melt phase. Solid state oxidation is another method for obtaining oxidized waxes from high molecular weight polyolefin resins through chain degradation. (See, e.g., U.S. Pat. Nos. 5,401,811; 5,064,908; 3,322,711 and 7,622,031.) It is understood that the inventions disclosed herein are not limited to homopolymers and copolymers of ethylene. Also contemplated in the invention disclosed herein are other types of homopolymeric or copolymeric crystallizable poly-alpha-olefins, such as, homopolymers and copolymers of propylene, 1-butene, 4-methyl-1-pentene, 3-methyl-1-butene, 4,4-dimethyl-1-pentene, 3-methyl-1-pentene, 4-methyl-1-hexene, 5-ethyl-1-hexene, 6-methyl-1-heptene, 1-hexene, 1-heptene, 1-octene, 1-nonene, 1-decene, and the like. Also included are oxidized waxes formed by the Fischer-Tropsch process. While these linear polymethylenes are not technically polyolefins, their structure is practically identical to polyethylene. Such material may be safe and biocompatible. The matrix comprises a material with a high affinity for the preservative, such as for example benzalkonium chloride (BAK), and low affinity for a drug or other ophthalmological agent. In some embodiments, the porous OxPO polymeric matrix exhibits a high affinity for the preservative, such that at least 50 percent of the preservative may be removed and at least 50 percent of the drug may be retained by the solution. In some embodiments, a matrix disposed within a nozzle may be a porous polymeric matrix.

The process of oxidation of an oxidized polyolefin may be characterized by an acid number. The progress of the oxidation can be determined by several methods, such acid number by titration or instrumental methods such as Fourier transform infrared (FTIR) spectroscopy or Near Infrared (NIR) spectroscopy. The porous polymeric matrix may comprise oxidized polyolefin (OxPO) microparticles with an acid value of about 30. The porous polymeric matrix may comprise an acid number of at least 4, from about 10 to about 50, from about 20 to about 40, etc. The porous polymeric matrix may comprise oxidized high density polyethylene with an acid value of about 30 mgKOH/g as measured by DIN EN ISO 2114.

An oxidized polyolefin may be characterized by a drop point, e.g. a melt point. A melt point of an oxidized polyolefin may relate to a chain length, a degree of oxidation, etc. The porous polymeric matrix may comprise oxidized polyolefin (OxPO) microparticles with a drop point between 125 and 135 Celsius. The porous polymeric matrix may comprise oxidized polyolefin (OxPO) microparticles with a drop point of about 50 to about 200° C., from about 100 to about 150° C., from about 125 to about 135° C., etc. The porous polymeric matrix may comprise oxidized high density polyethylene with a drop point between 125 and 135 Celsius as measured by DGF M-III 3.

An oxidized polyolefin may be characterized by a density. The density of the polymer may increase as the extent of oxidation increase. Without intending to be bound by theory, this may be the result of the substitution of heavier oxygen atoms for lighter hydrogen atoms in the polymer. An exact value in any instance may depend on the initial density of the starting polymer and the extent of oxidation. Density may measured by gradient column, for example, according to ASTM D1505-68 or -85, DIN 51579, etc. The porous polymeric matrix may comprise oxidized polyolefin (OxPO) microparticles with a density above about 0.910 g/cm3, from about 0.930 to about 1.210 or higher g/cm3, from about 0.940 to about 1.000 g/cm3, about 0.98, etc. The porous polymeric matrix may comprise oxidized high density polyethylene with a density of about 0.98 grams per cubic centimeter as measured by DIN 51579.

An oxidized polyolefin may be characterized by a viscosity. The viscosity of the polymer may vary with the degree of oxidation. For example, high molecular weight polyethylene of the feedstock may undergo oxidation to form polyethylene waxes of relatively lower molecular weight. The porous polymeric matrix may comprise oxidized polyolefin (OxPO) microparticles with a viscosity above about 100 microPascal seconds, between about 1 milliPascalseconds (mPas) and about 10 mPas, between about 2 mPas and about 6 mPas, and about 4 mPas. The porous polymeric matrix may comprise oxidized high density polyethylene with a density of about of 4.00 mPas at 190 Celsius as measured by DIN EN ISO3104.

In some embodiments, the matrix displays a high hydraulic permeability such that relatively little pressure is required to dispense a fluid. The hydraulic permeability may depend on the design of the filter. Larger pores may allow for higher flow for a given pressure drop. In some embodiments, hydraulic permeability is larger than about 0.01 Darcy. A nozzle may comprise a permeability of about 0.1 Darcy. A hydraulic permeability of 1 to 10 Darcy may allow fluid to be retained in the filter during instances when the pressure may be lowered subsequent to formation of a drop. A larger hydraulic permeability may allow the same plug to work for a wide range of formulations including, for example, high viscosity formulations, such as rewetting eye drops. In some embodiments, the porous polymeric matrix comprises a hydraulic permeability of, for example, 0.01 Da, 0.1 Da, 1 Da, 10 Da, 100 Da, 1000 Da or a hydraulic permeability within a range defined by any two of the preceding values.

In some embodiments, the matrix may be highly porous containing large channels through which liquid can flow. The pore or channel size in the matrix may be small enough so that the molecules, which may initially be far from the surface of the polymer in the matrix, may diffuse towards the polymer and adsorb. A matrix may comprise large interconnected pores or channels which may allow flow of solution and adsorption of the preservative into the pores or channels. The matrix may be formed as a porous gel, as a packed bed, and/or a structure formed by 3D printing soft lithography, electrospinning, or any other appropriate method. In some embodiments, the matrix may comprise a microporous gel. In some embodiments, the matrix comprises a packed bed of OxPO polymeric particles. The particles may be macroporous. The particles may be spherical or non-spherical. In some embodiments, the polymeric matrix may comprise nano-sized or micron-sized polymeric particles (e.g., nanogels or microgels).

In some embodiments, the particles may need to be stably held in the nozzle from which the formulation elutes from a container and thereby prevented from eluting from the nozzle. In some cases, the matrix may be sintered to fuse the particulate plug into porous monolith. In some cases, the device may have a cartridge or other assembly to retain the matrix in the nozzle. The device may have a solution permeable bag to retain the matrix. The device may comprise solid walls with a solution permeable bottom. The device may comprise entrance and exit faces with a matrix material therebetween. The entrance and exit faces may comprise solution permeable membranes. The entry and exit faces may comprise a filter. The entrance and exit faces may comprise a screen. The particles may be attached to the container walls through long polymeric chains and/or by placing a filter at the exit from the device. The device may comprise a packaging for delivery to a patient. The packaging may secure the device such that the device may not be compressed until the device is delivered to the patient. The packaging may secure the exit face from allowing the formulation to exit the bottle. The packaging may comprise a removable cap, a break-off cap, a resealable cap, etc.

In certain embodiments, particles described herein have an average largest dimension from about 1 nm to about 10 μm, about 1 nm to about 5 μm, about 1 nm to about 2 μm, about 1 nm to about 1 μm, about 1 nm to about 900 nm, about 1 nm to about 800 nm, about 1 nm to about 700, about 1 nm to about 600 nm, about 1 nm to about 500 nm, about 1 nm to about 400 nm, about 1 nm to about 300 nm, about 1 nm to about 200 nm, or even from about 1 nm to about 100 nm. In certain embodiments, the average largest dimension is the average largest diameter or the average equivalent diameter.

In certain embodiments, greater than 80%, greater than 90% or greater than 95% of the particles in the formulation have an average largest particle diameter of from about 1 nm to about 10 μm, about 1 nm to about 5 μm, about 1 nm to about 2 μm, about 1 nm to about 1 μm, about 1 nm to about 900 nm, about 1 nm to about 800 nm, about 1 nm to about 700 nm, about 1 nm to about 600 nm, about 1 nm to about 500 nm, about 1 nm to about 400 nm, about 1 nm to about 300 nm, about 1 nm to about 200 nm, or even from about 1 nm to about 100 nm. In certain embodiments, the average diameter is the average largest diameter or the average equivalent diameter.

In certain embodiments, particles described herein have an average diameter from about 100 nm to about 10 μm, about 100 nm to about 5 µm, about 100 nm to about 2 µm, about 100 nm to about 1 µm, about 100 nm to about 900 nm, about 100 nm to about 800 nm, about 100 nm to about 700 nm, about 100 nm to about 600 nm, about 200 nm to about 500 nm, about 250 nm to about 600 nm, about 300 nm to about 600 nm, about 350 nm to about 700 nm, about 450 nm to about 550 nm, about 475 nm to about 525 nm, or from about 400 nm to about 700 nm. In certain embodiments, the average diameter is the average largest diameter or the average equivalent diameter.

In certain embodiments, greater than 80%, greater than 90% or greater than 95% of the particles in the formulation have an average diameter from about 100 nm to about 10 µm, about 100 nm to about 5 µm, about 100 nm to about 2 µm, about 100 nm to about 1 µm, about 100 nm to about 900 nm, about 100 nm to about 800 nm, about 100 nm to about 700 nm, about 100 nm to about 600 nm, about 200 nm to about 500 nm, about 250 nm to about 600 nm, about 300 nm to about 600 nm, about 350 nm to about 700 nm, about 450 nm to about 550 nm, about 475 nm to about 525 nm, or from about 400 nm to about 700 nm. In certain embodiments, the average diameter is the average largest diameter or the average equivalent diameter.

The matrix may comprise a tortuosity such that the flow path of a solution, emulsion, or suspension through the nozzle may be significantly increased. In an embodiment where the matrix is a packed bed of macroporous particles, the packed beds of macroporous particles may have two or three levels of porosity: the space between the particles, the macropores in the particles, and the inherent porosity of the polymer. In some embodiments, all levels of porosity may contribute to the tortuosity of the matrix.

Therapeutic Agent

Embodiments of the present disclosure provide at least one therapeutic agent for delivery to an eye. A therapeutic agent is integrated into a fluid, which flows from a container through a nozzle comprising a porous polymeric matrix comprising oxidized polyolefin (OxPO) microparticles to an eye. In some embodiments, the fluid may comprise a solution, emulsion, or suspension comprising at least one therapeutic agent. The solution, emulsion, or suspension may comprise more than one therapeutic agent.

Example therapeutic agents which may be used in conjunction with a nozzle comprising a porous polymeric matrix comprising oxidized polyolefin (OxPO) microparticles include but are not limited to: timolol, dorzolamide, dexamethoasone phosphate, dexamethasone, Betimol®, olopatadine, brimonidine, tetrahydrozoline, latanoprostene bunod, latanoprost, and combinations of thereof. Therapeutic agents may comprise brand name drugs and formulations including, but not limited to, Timoptic, Xalatan, Combigan, Lumigan, Pataday, Pazeo, Trusopt, Cosopt, Alphagan, Visine, Vyzulta, Veseneo, and other agents described herein such as in the following tables. The therapeutic agents may be dissolved in aqueous solution. The solution may be sterilized and buffered to appropriate pH. In some embodiments, the solution may comprise inactive ingredients such as sodium chloride, sodium citrate, hydroxyethyl cellulose, sodium phosphate, citric acid, sodium dihydrogen phosphate, polyoxyl 40 hydrogenated castor oil, tromethamine, boric acid, mannitol, edetate disodium, sodium hydroxide, and/or hydrochloric acid. In some embodiments, the fluid comprises a preservative in addition to a therapeutic agent. Example preservatives include but are not limited to: benzalkonium chloride (BAK), alcohols, parabens, methyl paraben, propylparaben, EDTA, chlorhexidine, quaternary ammonium compounds, Purite®, stabilized oxychloro complexes, Sofzia®, sorbic acid, Sodium perborate, polyquaternium-1, chlorobutanol, cetrimonium chloride, edetate disodium, etc. In some embodiments, the preservative is benzalkonium chloride (BAK). In some embodiments, the preservative is quaternary ammonium compounds. In some embodiments, the preservative is polyquaternium-1. In some embodiments, the preservative is cetrimonium chloride.

Therapeutic agents for the treatment of, for example, dry eye, bacterial infection, glaucoma, hypertension, inflammation, allergic conjunctivitis, hypotrichosis of the eyelashes, fungal infection, etc. and therapeutic agents used for local anesthetic, pupil dilation, etc. may be administered to a patient as a solution, emulsion, or suspension delivered to an eye topically via a dropper bottle or similar delivery mechanism. The solution, emulsion, or suspension may be subject to contamination such as microbial, fungal, or particulate contamination, which may be adverse to patient health. In order to prevent such contamination a preservative may be added to the solution, emulsion, or suspension; however, patient exposure to preservatives may have adverse effects to eye health.

The present disclosure provides one or more therapeutic agents formulated with a preservative capable of being removed by a preservative removing device of the present disclosure. Therapeutic agents may comprise compounds and salts, for use in the treatment of ophthalmic diseases. The disclosed compounds and salts can be used, for example, for the treatment or prevention of vision disorders and/or for use during ophthalmological procedures for the prevention and/or treatment of ophthalmic disorders. The following list of examples are not intended to be limiting.

In some embodiments, the at least one therapeutic agent to be dispensed comprises an active ingredient selected from cyclosporine and lifitegrast. In some embodiments, the therapeutic agent may be an active ingredient in the treatment of dry eye.

In some embodiments, the at least one therapeutic agent to be dispensed comprises an active ingredient selected from sulfacetamide sodium, ofloxacin, gatifloxacin, ciprofloxacin, moxifloxacin, tobramycin, levofloxacin, prednisolone acetate, polymyxin B sulfate, and trimethoprim. In some embodiments, the therapeutic formulation to be dispensed comprises the active ingredients sulfacetamide sodium and prednisolone acetate. In some embodiments, the therapeutic formulation to be dispensed comprises the active ingredients polymyxin B sulfate and trimethoprim. In some embodiments, the therapeutic agent may be an active ingredient in the treatment of a bacterial infection.

In some embodiments, the at least one therapeutic agent to be dispensed comprises an active ingredient selected from brimonidine tartrate, bimatoprost, levobunolol hydrochloride, brinzolamide, betaxolol hydrochloride, pilocarpine hydrochloride, apraclonidine, travoprost, timolol maleate, latanoprost, dorzolamide hydrochloride, and tafluprost. In some embodiments, the therapeutic formulation to be dispensed comprises the active ingredients brimonidine tartrate and timolol maleate. In some embodiments, the therapeutic formulation to be dispensed comprises the active ingredients brinzolamide and brimonidine tartrate. In some embodiments, the therapeutic agent may be an active ingredient in the treatment of glaucoma or hypertension.

In some embodiments, the at least one therapeutic agent to be dispensed comprises an active ingredient selected from ketorolac tromethamine, fluorometholone, prednisolone acetate, difluprednate, fluorometholone acetate, nepafenac, dexamethasone, diclofenac sodium, bromfenac, gentamicin, tobramycin, neomycin, and polymyxin B sulfate. In some embodiments, the therapeutic formulation to be dispensed comprises the active ingredients gentamicin and prednisolone acetate. In some embodiments, the therapeutic formulation to be dispensed comprises the active ingredients tobramycin and dexamethasone. In some embodiments, the therapeutic formulation to be dispensed comprises the active ingredients neomycin, polymyxin B sulfate and dexamethasone. In some embodiments, the therapeutic agent may be an active ingredient in the treatment of inflammation.

In some embodiments, the at least one therapeutic agent to be dispensed comprises an active ingredient selected from nedocromil sodium, epinastine HCl, alcaftadine, lodoxamide tromethamine, emedastine difumarate, and olopatadine hydrochloride. In some embodiments, the therapeutic agent may be an active ingredient in the treatment of allergic conjunctivitis.

In some embodiments, the at least one therapeutic agent to be dispensed comprises an active ingredient selected from proparacaine hydrochloride and tetracaine hydrochloride. In some embodiments, the therapeutic agent may be a local anesthetic.

In some embodiments, the at least one therapeutic agent to be dispensed comprises an active ingredient selected from cyclopentolate hydrochloride, atropine sulfate, and tropicamide. In some embodiments, the therapeutic formulation to be dispensed comprises the active ingredients cyclopentolate hydrochloride and phenylephrine hydrochloride. In such embodiments, the therapeutic agent may dilate pupils.

In some embodiments, the at least one therapeutic agent to be dispensed comprises the active ingredient natamycin. In such embodiments, the therapeutic agent may be an active ingredient in the treatment of fungal infection.

In some embodiments, the at least one therapeutic agent to be dispensed comprises an active ingredient selected from lipoic acid choline ester chloride, rebamipide, pilocarpine, aceclidine, tropicamide, sodium hyaluronate, diclofenac sodium, pilocarpine HCl, and ketorolac. In some embodiments, the therapeutic formulation to be dispensed comprises the active ingredients aceclidine and tropicamide. In some embodiments, the therapeutic formulation to be dispensed comprises the active ingredients sodium hyaluronate and diclofenac sodium and pilocarpine HCl. In some embodiments, the therapeutic formulation to be dispensed comprises the active ingredients pilocarpine and ketorolac. In some embodiments, the therapeutic agent may be an active ingredient in the treatment of presbyopia.

In some embodiments, the at least one therapeutic agent to be dispensed is a therapeutic agent selected from Tables 1 to 4.

TABLE 1

Therapeutic Agent Sorted by Indication

| Market Name | Drug | % Active Ingredient | Formulation Type | Indication | Preservative |
|---|---|---|---|---|---|
| Dry Eye | | | | | |
| Restasis | Cyclosporine | 0.05% | emulsion | keratoconjunctivitis sicca | none |
| Xiidra | Lifitegrast | 5% | solution | keratoconjunctivitis sicca | none |
| Visine | Tetrahydrozoline | | | keratoconjunctivitis sicca | |
| Bacterial Infection | | | | | |
| Bleph 10 | sulfacetamide sodium | 10% | solution | conjunctivitis and other ocular infections | benzalkonium chloride 0.005% |
| Blephamide | sulfacetamide sodium— prednisolone acetate | 10%/0.2% | suspension | bacterial ocular infection | benzalkonium chloride 0.004% |
| Ocuflox | Ofloxacin | 0.3% | solution | bacterial ocular infection; corneal ulcers | benzalkonium chloride (0.005%) |
| Polytrim | polymyxin B sulfate and trimethoprim | polymyxin B sulfate 10,000 units/mL; trimethoprim sulfate equivalent to 1 mg/mL | solution | ocular bacterial infections; conjunctivitis; blepharo- conjunctivitis | benzalkonium chloride 0.04 mg/mL |
| Zymaxid | Gatifloxacin | 0.3% and 0.5% | solution | bacterial conjunctivitis | benzalkonium chloride 0.005% |
| Zymar | Gatifloxacin | 0.3% | solution | bacterial conjunctivitis | benzalkonium chloride 0.005%; |
| Ciloxan | Ciprofloxacin | 0.3% | solution | bacterial conjunctivitis | None |
| Moxeza | Moxifloxacin | 0.5% | solution | bacterial conjunctivitis | none |
| Tobrex | Tobramycin | 0.3% | solution | infections of the eye and its adnexa caused by susceptible bacteria | benzalkonium chloride 0.01% |

TABLE 1-continued

Therapeutic Agent Sorted by Indication

| Market Name | Drug | % Active Ingredient | Formulation Type | Indication | Preservative |
|---|---|---|---|---|---|
| Vigamox | Moxifloxacin | 0.5% | solution | bacterial conjunctivitis | none |
| Iquix | Levofloxacin | 1.5% | solution | bacterial conjunctivitis | benzalkonium chloride 0.005% |
| Quixin | Levofloxacin | 0.5% | solution | bacterial conjunctivitis | benzalkonium chloride 0.005% |
| Glaucoma or Hypertension | | | | | |
| Alphagan | brimonidine tartrate | 0.01% | solution | open-angle glaucoma or ocular hypertension | Purite ® 0.005% (0.05 mg/mL) |
| Lumigan | Bimatoprost | 0.01% | solution | open angle glaucoma or ocular hypertension | benzalkonium chloride 0.2 mg/mL |
| Betagan | levobunolol hydrochloride | 0.5% | solution | chronic open-angle glaucoma or ocular hypertension | benzalkonium chloride 0.004% |
| Combigan | brimonidine tartrate/timolol maleate | 0.2%/0.5% | solution | glaucoma or ocular hypertension who require adjunctive or replacement therapy due to inadequately controlled IOP | benzalkonium chloride 0.005% |
| Azopt | Brinzolamide | 1% | suspension | ocular hypertension or open-angle glaucoma | benzalkonium chloride 0.1 mg |
| Betoptic S | betaxolol hydrochloride | 0.25% and 0.5% | suspension | ocular hypertension or chronic open angle glaucoma | benzalkonium chloride 0.1 mg in 1 mL |
| Isopto Carpine | pilocarpine hydrochloride | 1%, 2% and 4% | solution | IOP reduction; open-angle glaucoma or ocular hypertension; acute angle-closure glaucoma; induction of miosis | benzalkonium chloride 0.01% |
| Iopidine | Apraclonidine | 0.5% and 1.0% | solution | Short term adjunctive therapy in patients on maximally tolerated medical therapy who require additional IOP reduction | benzalkonium chloride 0.01% |
| Simbrinza | brinzolamide/ brimonidine tartrate | 1%/0.2% | suspension | reduction of elevated IOP in patients with open-angle glaucoma or ocular hypertension | benzalkonium chloride 0.03 mg |
| Travatan Z | Travoprost | 0.004% | solution | open-angle glaucoma or ocular hypertension who are intolerant of other intraocular pressure lowering medications | ionic buffered system, sofZia |
| Isralol | Timolol maleate | 0.5% | solution | ocular hypertension or open-angle glaucoma | benzalkonium chloride 0.05 mg/mL |
| Xalatan | Latanoprost | approximately 1.5 µg per drop | solution | open-angle glaucoma or ocular hypertension | benzalkonium chloride, 0.02% |
| Trusopt | dorzolamide hydrochloride | 2% | solution | ocular hypertension or open-angle glaucoma | benzalkonium chloride 0.0075% |
| Timoptic | timolol maleate | 0.25% and 0.5% | solution | ocular hypertension or open-angle glaucoma | benzalkonium chloride |
| Ziotan | Tafluprost | 0.0015% | solution | open-angle glaucoma or ocular hypertension | none |
| Vesneo | Latanoprostene Bunod | | | glaucoma | |

TABLE 1-continued

Therapeutic Agent Sorted by Indication

| Market Name | Drug | % Active Ingredient | Formulation Type | Indication | Preservative |
|---|---|---|---|---|---|
| Vyzulta | Latanoprostene Bunod | | | glaucoma | |
| Cosopt | Dorzolamide + Timolol | | | Glaucoma | |
| | | | Inflammation | | |
| Acular LS | ketorolac tromethamine | 0.4% | solution | ocular pain and burning/stinging following corneal refractive surgery | benzalkonium chloride 0.006% |
| Acular | ketorolac tromethamine | 0.5% | solution | inflammation following cataract surgery; relief of ocular itching due to seasonal allergic conjunctivitis | benzalkonium chloride 0.01% |
| Acuvail | ketorolac tromethamine | 0.45% | solution | treatment of pain and inflammation following cataract surgery | none |
| FML Forte | Fluorometholone | 0.25% | ointment | corticosteroid-responsive inflammation of the palpebral and bulbar conjunctiva, cornea and anterior segment of the globe | benzalkonium chloride 0.005% |
| FML | Fluorometholone | 0.1% | suspension | corticosteroid-responsive inflammation of the palpebral and bulbar conjunctiva, cornea and anterior segment of the globe | benzalkonium chloride 0.004% |
| Pred Forte | prednisolone acetate | 1% | suspension | steroid-responsive inflammation of the palpebral and bulbar conjunctiva, cornea, and anterior segment of the globe | benzalkonium chloride |
| Pred Mild | prednisolone acetate | 0.12% | suspension | mild to moderate noninfectious allergic and inflammatory disorders of the lid, conjunctiva, cornea, and sclera, including chemical and thermal burns | benzalkonium chloride |
| Pred-G | gentamicin and prednisolone acetate | 0.3%/1% | suspension | steroid-responsive inflammatory; bacterial infection; thermal burns or penetration of foreign bodies | Benzalkonium chloride 0.005% |
| Durezol | Difluprednate | 0.05% | emulsion | inflammation and pain associated with ocular surgery | sorbic acid 0.1% |
| Flarex | fluorometholone acetate | 0.1% | suspension | steroid-responsive inflammatory conditions of the palpebral and bulbar conjunctiva, cornea and anterior segment of the eye | benzalkonium chloride 0.01% |
| Ilevro | Nepafenac | 0.3% | suspension | pain and inflammation associated with cataract surgery | benzalkonium chloride 0.005% |
| Maxidex | Dexamethasone | 0.1% | suspension | Steroid responsive inflammatory conditions; corneal injury from chemical, radiation, or thermal burns, or penetration of foreign bodies | benzalkonium chloride 0.01% |

TABLE 1-continued

Therapeutic Agent Sorted by Indication

| Market Name | Drug | % Active Ingredient | Formulation Type | Indication | Preservative |
|---|---|---|---|---|---|
| Maxitrol | neomycin and polymyxin B sulfates and dexamethasone | neomycin sulfate equivalent to neomycin 3.5 mg, polymyxin B sulfate 10,000 units, dexamethasone 0.1% | solution | steroid-responsive inflammatory ocular conditions for which a corticosteroid is indicated and where bacterial infection or a risk of bacterial ocular infection exists | methylparaben 0.05%, propylparaben 0.01% |
| Nevanac | Nepafenac | 0.1% | suspension | pain and inflammation associated with cataract surgery | benzalkonium chloride 0.005% |
| Omnipred | prednisolone acetate | 1.0% | suspension | steroid responsive inflammatory conditions; corneal injury from chemical, radiation, or thermal of foreign bodies | benzalkonium chloride 0.01% |
| Tobradex ST | tobramycin/ dexamethasone | 0.3%/0.05% | suspension | steroid-responsive inflammatory ocular conditions for which a corticosteroid is indicated and where superficial bacterial ocular infection exists | benzalkonium chloride 0.1 mg |
| Voltaren Ophthalmic | diclofenac sodium | 0.1% | solution | inflammation from cataract extraction; temporary relief of pain and photophobia following corneal refractive surgery | None |
| Bromday | Bromfenac | 0.09% | solution | postoperative inflammation in patients who have undergone cataract extraction | benzalkonium chloride 0.05 mg/mL |
| Xibrom | Bromfenac | 0.09% | solution | postoperative inflammation in patients who have undergone cataract extraction | benzalkonium chloride (0.05 mg/mL) |
| Xibrom | Bromfenac | 0.09% | solution | postoperative inflammation in patients who have undergone cataract extraction | benzalkonium chloride 0.05 mg/mL |
| Allergic Conjunctivitis | | | | | |
| Alocril | nedocromil sodium | 2% | solution | itching associated with allergic conjunctivitis | benzalkonium chloride 0.01% |
| Elestat | epinastine HCl | 0.05% | suspension | itching associated with allergic conjunctivitis | Benzalkonium chloride 0.01%; |
| Lastacaft | Alcaftadine | 0.25% | solution | itching associated with allergic conjunctivitis | benzalkonium chloride 0.005% |
| Alomide | lodoxamide tromethamine | 0.1% | solution | vernal keratoconjunctivitis; giant papillary conjunctivitis; allergic/atopic conjunctivitis | benzalkonium chloride 0.007% w/v |
| Emadine | emedastine difumarate | 0.5% | solution | allergic conjunctivitis | benzalkonium chloride, 0.01% |
| Pataday | olopatadine hydrochloride | 0.2% | solution | ocular itching associated with allergic conjunctivitis | benzalkonium chloride 0.01% |
| Pazeo | olopatadine hydrochloride | 0.7% | solution | ocular itching associated with allergic conjunctivitis | benzalkonium chloride 0.015% |

TABLE 1-continued

Therapeutic Agent Sorted by Indication

| Market Name | Drug | % Active Ingredient | Formulation Type | Indication | Preservative |
|---|---|---|---|---|---|
| Hair Growth | | | | | |
| Latisse | Bimatoprost | 0.03% | solution | hypotrichosis of the eyelashes | benzalkonium chloride 0.05 mg/mL |
| Local Anesthetic | | | | | |
| Alcaine | proparacaine hydrochloride | 0.5% | solution | topical anesthesia—removal of foreign bodies; measurement of intraocular pressure; conjunctive scraping | benzalkonium chloride 0.01% |
| Tetracaine | Tetracaine hydrochloride | 0.5% | solution | procedures requiring a rapid and short acting topical ophthalmic anesthetic | None |
| Pupil Dilation | | | | | |
| Cyclogyl | cyclopentolate hydrochloride | 0.5%, 1.0% or 2.0% | solution | pre- and post-operative states when mydriasis is required and when a shorter acting mydriatic and cycloplegic is needed in the therapy of iridocyclitis | Benzalkonium chloride 0.1 mg in 1.0 mL |
| Cyclomydril | cyclopentolate hydrochloride and phenylephrine hydrochloride | 0.2%/1.0% | solution | For the production of mydriasis (pupil dilation) | Benzalkonium chloride 0.01% |
| Isopto Atropine | atropine sulfate | 1% | solution | mydriasis; cycloplegia; penalization of the healthy eye in the treatment of amblyopia | benzalkonium chloride 0.01% |
| Mydriacyl | Tropicamide | 0.5% or 1.0% | solution | mydriasis and cycloplegia | benzalkonium chloride 0.01% |
| Fungal infection | | | | | |
| Natacyn | Natamycin | 5% | suspension | anti-fungal; fungal blepharitis, conjunctivitis, and keratitis | benzalkonium chloride 0.02% |

TABLE 2

Presbyopia Formulations

| Drug Code | Drug | % Active Ingredient | Formulation Type | Indication | Preservative |
|---|---|---|---|---|---|
| Presbyopia | | | | | |
| EV06/ UNR844 | lipoic acid choline ester chloride | 3.0% | solution | presbyopia | benzalkonium chloride, 0.01% |
| PRX-100 | aceclidine/ tropicamide | 0.25-2.0%/ 0.025-0.1% | Solution or suspension | presbyopia | benzalkonium chloride, 0.02% |
| CSF-1 | sodium hyaluronate/ diclofenac sodium/ pilocarpine HCl | 0.1-0.9%/ 0.006-0.012%/ 0.2-0.4% | Solution or suspension | presbyopia | Any, benzalkonium chloride, 0.01% |

TABLE 2-continued

| | | Presbyopia Formulations | | | |
|---|---|---|---|---|---|
| Drug Code | Drug | % Active Ingredient Presbyopia | Formulation Type | Indication | Preservative |
| AAGN-199201 | Pilocarpine and/or oxymetazoline | 0.1%-1% | Solution or suspension | presbyopia | Any, benzalkonium chloride, 0.01% |
| AAGN-190584 | keterolac | 0.1%-1% | Solution or suspension | presbyopia | Any, benzalkonium chloride, 0.01% |

TABLE 3

| | Additional Therapeutic Agents | | | | |
|---|---|---|---|---|---|
| Market Name | Drug | % Active Ingredient | Formulation Type | Indication | Preservative |
| Restasis | cyclosporine | 0.05% | emulsion | keratoconjunctivitis sicca | none |
| Latisse | bimatoprost | 0.03% | solution | hypotrichosis of the eyelashes | benzalkonium chloride 0.05 mg/mL |
| Alphagan | brimonidine Tartrate | 0.01% | solution | open-angle glaucoma or ocular hypertension | Purite ® 0.005% (0.05 mg/mL) |
| Lumigan | bimatoprost | 0.01% | solution | open angle glaucoma or ocular hypertension | benzalkonium chloride 0.2 mg/mL |
| Acular LS | ketorolac tromethamine | 0.4% | solution | ocular pain and burning/stinging following corneal refractive surgery | benzalkonium chloride 0.006% |
| Acular | ketorolac tromethamine | 0.5% | solution | inflammation following cataract surgery; relief of ocular itching due to seasonal allergic conjunctivitis | benzalkonium chloride 0.01% |
| Acuvail | ketorolac tromethamine | 0.45% | solution | treatment of pain and inflammation following cataract surgery | none |
| Alocril | nedocromil sodium | 2% | solution | itching associated with allergic conjunctivitis | benzalkonium chloride 0.01% |
| Betagan | levobunolol hydrochloride | 0.5% | solution | chronic open-angle glaucoma or ocular hypertension | benzalkonium chloride 0.004% |
| Bleph 10 | sulfacetamide sodium | 10% | solution | conjunctivitis and other ocular infections | benzalkonium chloride 0.005% |
| Blephamide | sulfacetamide sodium— prednisolone acetate | 10%/0.2% | suspension | bacterial ocular infection | benzalkonium chloride 0.004% |
| Combigan | brimonidine tartrate/timolol maleate | 0.2%/0.5% | solution | glaucoma or ocular hypertension who require adjunctive or replacement therapy due to inadequately controlled iop | benzalkonium chloride 0.005% |
| Elestat | epinastine HCl | 0.05% | suspension | itching associated with allergic conjunctivitis | benzalkonium chloride 0.01%; |
| FML Forte | fluorometholone | 0.25% | ointment | corticosteroid-responsive inflammation of the palpebral and bulbar conjunctiva, cornea and anterior segment of the globe | benzalkonium chloride 0.005% |

TABLE 3-continued

Additional Therapeutic Agents

| Market Name | Drug | % Active Ingredient | Formulation Type | Indication | Preservative |
|---|---|---|---|---|---|
| FML | fluorometholone | 0.1% | suspension | corticosteroid-responsive inflammation of the palpebral and bulbar conjunctiva, cornea and anterior segment of the globe | benzalkonium chloride 0.004% |
| Lastacaft | alcaftadine | 0.25% | solution | itching associated with allergic conjunctivitis | benzalkonium chloride 0.005% |
| Ocuflox | ofloxacin | 0.3% | solution | bacterial ocular infection; corneal ulcers | benzalkonium chloride (0.005%) |
| Polytrim | polymyxin B sulfate and trimethoprim | polymyxin B sulfate 10,000 units/mL; trimethoprim sulfate equivalent to 1 mg/mL | solution | ocular bacterial infections; conjunctivitis; blepharo-conjunctivitis | benzalkonium chloride 0.04 mg/mL |
| Pred Forte | prednisolone acetate | 1% | suspension | steroid-responsive inflammation of the palpebral and bulbar conjunctiva, cornea, and anterior segment of the globe | benzalkonium chloride |
| Pred Mild | prednisolone acetate | 0.12% | suspension | mild to moderate noninfectious allergic and inflammatory disorders of the lid, conjunctiva, cornea, and sclera, including chemical and thermal burns | benzalkonium chloride |
| Pred-G | gentamicin and prednisolone acetate | 0.3%/1% | suspension | steroid-responsive inflammatory; bacterial infection; thermal burns or penetration of foreign bodies | benzalkonium chloride 0.005% |
| Zymaxid | gatifloxacin | 0.3% and 0.5% | solution | bacterial conjunctivitis | benzalkonium chloride 0.005% |
| Zymar | gatifloxacin | 0.3% | solution | bacterial conjunctivitis | benzalkonium chloride 0.005%; |
| Alcaine | proparacaine hydrochloride | 0.5% | solution | topical anesthesia—removal of foreign bodies; measurement of intraocular pressure; conjunctive scraping | benzalkonium chloride 0.01% |
| Alomide | lodoxamide tromethamine | 0.1% | solution | vernal keratoconjunctivitis; giant papillary conjunctivitis; allergic/atopic conjunctivitis | benzalkonium chloride 0.007% w/v |
| Azopt | brinzolamide | 1% | suspension | ocular hypertension or open-angle glaucoma | benzalkonium chloride 0.1 mg |
| Betoptic S | betaxolol hydrochloride | 0.25% and 0.5% | suspension | ocular hypertension or chronic open angle glaucoma | benzalkonium chloride 0.1 mg in 1 mL |
| Ciloxan | ciprofloxacin | 0.3% | solution | bacterial conjunctivitis | None |
| Cyclogyl | cyclopentolate hydrochloride | 0.5%, 1.0% or 2.0% | solution | pre- and post-operative states when mydriasis is required and when a shorter acting mydriatic and cycloplegic is needed in the therapy of iridocyclitis | benzalkonium chloride 0.1 mg in 1.0 mL |

TABLE 3-continued

Additional Therapeutic Agents

| Market Name | Drug | % Active Ingredient | Formulation Type | Indication | Preservative |
|---|---|---|---|---|---|
| Cyclomydril | cyclopentolate hydrochloride and phenylephrine hydrochloride | 0.2%/1.0% | solution | for the production of mydriasis (pupil dilation) | benzalkonium chloride 0.01% |
| Durezol | difluprednate | 0.05% | emulsion | inflammation and pain associated with ocular surgery | sorbic acid 0.1% |
| Emadine | emedastine difumarate | 0.5% | solution | allergic conjunctivitis | benzalkonium chloride, 0.01% |
| Flarex | fluorometholone acetate | 0.1% | suspension | steroid-responsive inflammatory conditions of the palpebral and bulbar conjunctiva, cornea and anterior segment of the eye | benzalkonium chloride 0.01% |
| Ilevro | nepafenac | 0.3% | suspension | pain and inflammation associated with cataract surgery | benzalkonium chloride 0.005% |
| Iopidine | apraclonidine | 0.5% and 1.0% | solution | short term adjunctive therapy in patients on maximally tolerated medical therapy who require additional iop reduction | benzalkonium chloride 0.01% |
| Isopto Atropine | atropine sulfate | 1% | solution | mydriasis; cycloplegia; penalization of the healthy eye in the treatment of amblyopia | benzalkonium chloride 0.01% |
| Isopto Carpine | pilocarpine hydrochloride | 1%, 2% and 4% | solution | iop reduction; open-angle glaucoma or ocular hypertension; acute angle-closure glaucoma; induction of miosis | benzalkonium chloride 0.01% |
| Maxidex | dexamethasone | 0.1% | suspension | steroid responsive inflammatory conditions; corneal injury from chemical, radiation, or thermal burns, or penetration of foreign bodies | benzalkonium chloride 0.01% |
| Maxitrol | neomycin and polymyxin B sulfates and dexamethasone | neomycin sulfate equivalent to neomycin 3.5 mg, polymyxin B sulfate 10,000 units, dexamethasone 0.1% | solution | steroid-responsive inflammatory ocular conditions for which a corticosteroid is indicated and where bacterial infection or a risk of bacterial ocular infection exists | methylparaben 0.05%, propylparaben 0.01% |
| Moxeza | moxifloxacin | 0.5% | solution | bacterial conjunctivitis | None |
| Mydriacyl | tropicamide | 0.5% or 1.0% | solution | mydriasis and cycloplegia | benzalkonium chloride 0.01% |
| Natacyn | natamycin | 5% | suspension | anti-fungal; fungal blepharitis, conjunctivitis, and keratitis | benzalkonium chloride 0.02% |
| Nevanac | nepafenac | 0.1% | suspension | pain and inflammation associated with cataract surgery | benzalkonium chloride 0.005% |
| Omnipred | prednisolone acetate | 1.0% | suspension | steroid responsive inflammatory conditions; corneal injury from chemical, radiation, or thermal burns, or penetration of foreign bodies | benzalkonium chloride 0.01% |

TABLE 3-continued

Additional Therapeutic Agents

| Market Name | Drug | % Active Ingredient | Formulation Type | Indication | Preservative |
|---|---|---|---|---|---|
| Pataday | olopatadine hydrochloride | 0.2% | solution | ocular itching associated with allergic conjunctivitis | benzalkonium chloride 0.01% |
| Pazeo | olopatadine hydrochloride | 0.7% | solution | ocular itching associated with allergic conjunctivitis | benzalkonium chloride 0.015% |
| Simbrinza | brinzolamide/ brimonidine tartrate | 1%/0.2% | suspension | reduction of elevated iop in patients with open-angle glaucoma or ocular hypertension | benzalkonium chloride 0.03 mg |
| Tetracaine | hydrochloride | 0.5% | solution | procedures requiring a rapid and shortacting topical ophthalmic anesthetic | None |
| Tobradex ST | tobramycin/ dexamethasone | 0.3%/0.05% | suspension | steroid-responsive inflammatory ocular conditions for which a corticosteroid is indicated and where superficial bacterial ocular infection exists | benzalkonium chloride 0.1 mg |
| Tobrex | tobramycin | 0.3% | solution | infections of the eye and its adnexa caused by susceptible bacteria | benzalkonium chloride 0.01% |
| Travatan Z | travoprost | 0.004% | solution | open-angle glaucoma or ocular hypertension who are intolerant of other intraocular pressure lowering medications | ionic buffered system, sofZia |
| Vigamox | moxifloxacin | 0.5% | solution | bacterial conjunctivitis | None |
| Voltaren Ophthalmic | diclofenac sodium | 0.1% | solution | inflammation from cataract extraction; temporary relief of pain and photophobia following corneal refractive surgery | None |
| Trusopt | dorzolamide hydrochloride | 2% | solution | ocular hypertension or open-angle glaucoma | benzalkonium chloride 0.0075% |
| Timoptic | timolol maleate | 0.25% and 0.5% | solution | ocular hypertension or open-angle glaucoma | benzalkonium chloride |
| Ziotan | tafluprost | 0.0015% | solution | open-angle glaucoma or ocular hypertension | none |
| Xalatan | latanoprost | approximately 1.5 µg per drop | solution | open-angle glaucoma or ocular hypertension | benzalkonium chloride, 0.02% |
| Bromday | bromfenac | 0.09% | solution | postoperative inflammation in patients who have undergone cataract extraction | benzalkonium chloride 0.05 mg/mL |
| Isralol | timolol maleate | 0.5% | solution | ocular hypertension or open-angle glaucoma | benzalkonium chloride 0.05 mg/mL |
| Xibrom | bromfenac | 0.09% | solution | postoperative inflammation in patients who have undergone cataract extraction | benzalkonium chloride (0.05 mg/mL) |
| Iquix | levofloxacin | 1.5% | solution | bacterial conjunctivitis | benzalkonium chloride 0.005% |
| Quixin | levofloxacin | 0.5% | solution | bacterial conjunctivitis | benzalkonium chloride 0.005% |

TABLE 3-continued

Additional Therapeutic Agents

| Market Name | Drug | % Active Ingredient | Formulation Type | Indication | Preservative |
|---|---|---|---|---|---|
| Xibrom | bromfenac | 0.09% | solution | postoperative inflammation in patients who have undergone cataract extraction | benzalkonium chloride 0.05 mg/mL |
| Xiidra | lifitegrast | 5% | solution | Dry Eye | None |

TABLE 4

Other Therapeutic Agents

| Code of Drug in Clinical Trial | Drug | % Active Ingredient | Formulation Type | Indication | Preservative |
|---|---|---|---|---|---|
| EV06/ UNR844 | lipoic acid choline ester chloride | 3.0% | solution | presbyopia | benzalkonium chloride, 0.01% |
| PRX-100 | aceclidine/ tropicamide | 0.25-2.0%/ 0.025-0.1% | Solution or suspension | presbyopia | benzalkonium chloride, 0.02% |
| SF-1 | sodium hyaluronate/ diclofenac sodium/ pilocarpine HCl | 0.1-0.9%/ 0.006-0.012%/ 0.2-0.4% | Solution or suspension | presbyopia | Any, benzalkonium chloride, 0.01% |
| ECF843 | | 0.1%-1% | Solution or suspension | Dry eye | Any, benzalkonium chloride, 0.01% |
| None | rebamipide | 1%, 2% | solution | Dry eye (keratoconjunctivitis sicca) | Any, benzalkonium chloride, 0.01% |
| AAGN-199201 | Pilocarpine and/or oxymetazoline | 0.1%-1% | Solution or suspension | presbyopia | Any, benzalkonium chloride, 0.01% |
| AAGN-190584 | keterolac | 0.1%-1% | Solution or suspension | presbyopia | Any, benzalkonium chloride, 0.01% |
| | pilocarpine | 0.3% | Solution or suspension | presbyopia | Any, benzalkonium chloride, 0.01% |
| | pilocarpine | varies with severity of presbyopia, 0.3%-2.2% | Solution or suspension | presbyopia | Any, benzalkonium chloride, 0.01% |

Preservative

The present disclosure provides one or more preservatives for solutions, emulsions, or suspensions of therapeutic agents of the present disclosure. Preservatives may comprise compounds and salts, for use as preservatives for solutions, emulsions, or suspensions of therapeutic agents. The one or more preservatives may for example prevent microbial and/or fungal growth. The one or more preservatives may for example prevent physical or chemical deterioration of a therapeutic agent.

Non-limiting examples of preservative agents include benzalkonium chloride, ethylenediaminetetraacetic acid (EDTA), or the sodium salt of EDTA, chlorobutanol, phenylmercuric acetate, phenylmercuric nitrate, chlorhexidine acetate, thimerosal, benzethonium chloride, sorbic acid, alcohols, parabens (e.g., methylparaben, polyparaben), chlorhexidine, quaternary ammonium compounds, polyquaternium-1 (Polyquad®) Purite®, stabilized oxychloro complexes, Sofzia®, sodium perborate (GenAqua®), cetrimonium chloride, edetate disodium, etc. In some embodiments, the preservative is benzalkonium chloride. In some embodiments, the preservative is a quaternary ammonium compound. In some embodiments, the preservative is polyquaternium-1. In some embodiments, the preservative is cetrimonium chloride.

In some embodiments, the particulate plug may further include a preservative removing compound or a preservative deactivating compound. Preservative removing or deactivating compounds can decrease toxicity of a formulation to be delivered through typical separation methods including, but not limited to, adsorption, ion exchange, chemical precipitation, or solvent extraction. Preservative removing or deactivating compounds can include, but are not limited to, activated charcoal, antioxidants, ethylenediaminetetraacetic acid (EDTA), anionic hydrogels, cationic compounds, neutralizing agents, or combinations thereof.

The Purite® preservative system includes Stabilized Oxychloro Complex (SOC), a combination of chlorine dioxide, chlorite and chlorate. When exposed to light, SOC dissociates into water, oxygen, sodium and chlorine free radicals which cause oxidation of intracellular lipids and glutathione, interrupting vital enzymes for cell function and maintenance. For preservatives such as Purite® which produce chlorine free radicals, the particulate plug of the disclosure can include a material that has a high affinity for free radicals such as activated charcoal or antioxidants such as vitamin E.

The SofZia® preservative system in Travatan Z (Alcon Laboratories, Fort Worth, Tex.) contains borate, sorbitol, propylene glycol, and zinc. Without intending to be bound by theory, it is believed that the preservative effect is from a combination of borate and zinc. For preservatives including borate and zinc, such as SofZia®, the particulate plug of the disclosure can include a metal chelating agent such as EDTA, anionic hydrogels that can extract cationic zinc through electrostatic interactions, cationic hydrogels or resins that can extract anionic borate ions through electrostatic interactions, or a neutralizing agent that can neutralize boric acid.

The materials that can sequester the preservative can be incorporated into the particulate plug as microparticles, such as particles of activated charcoal. The microparticles can be packed into the particulate plug such that the liquid has sufficient space in between the particles to flow out, while also providing sufficient contact area for binding. Alternatively, the sequestering materials could be incorporated into particles of other suitable materials such as the polymer particles of the disclosure to facilitate the contact between the eluding formulation and the sequestering material. In some cases, the sequestration material, can be integrated into the polymer covalently. The sequestering material can be a nanoparticle or can be incorporated into a nanoparticle, which could in turn be dispersed into the polymer particles that form a packed bed in the tip. The nanoparticle could also be deposited just on the surface of the larger particles. The sequestering material could also form tubes that can be arranged in parallel to provide the path for liquid to flow out and sequestration to occur on the surface.

The materials present in the particulate plug to neutralize the free radicals in the formulation, for example, vitamins, can be incorporated into the polymer particles that form the particulate plug. Bases can be incorporated to bring the pH to a level that is comfortable in the eyes. The polymer particles can be loaded with vitamin E for example by soaking the particles in a solution of vitamin E dissolved in an organic liquid, leading to uptake of vitamin E into the particles. Subsequently, the organic liquid such as ethanol can be evaporated or extracted into water to form particles loaded with vitamin E. The material of the particles that is loaded with vitamin E could be chosen to achieve other beneficial purposes such as extraction of some other component of the preservative.

The preservative effect of the formulations can be improved by incorporation of another preservative such as Benzalkonium Chloride so that the formulation can pass EPA criterion as well. The added BAK or the other preservative can be removed by the particulate plug to achieve improved preservative performance without increasing toxicity.

The particulate plug including a preservative removing compound or preservative deactivating compound can be formed in various shapes such as spheres, cylinders, tubes, highly irregular, flat sheets etc, where the surface could be rough or smooth. The particles or other shapes integrated into the tip can contain some preservative to ensure that the tip itself remains sterile. The preservative pre-loaded into the tip could be loaded via adsorption or be chemically attached to the material through a bond. For example, Polyquaternium can be integrated into the polymer forming the particles. The covalent attachment will prevent diffusion of the pre-loaded preservative into the tear film. Alternatively, the pre-loaded preservative could be sufficiently large in molecular weight or have very low partitioning into the eluding formulation.

In cases wherein the particulate plug including a preservative removing compound or a preservative deactivating compound is intended to add a component to the eluding formulation, the amount of that material in the particulate plug will be sufficiently large to ensure that there is sufficient amount remaining for the entire bottle, or at least 90% of the bottle. In cases wherein the particulate plug including a preservative removing compound or a preservative deactivating compound is intended to sequester a component from the eluding formulation, the volume and area in the particulate plug will be sufficiently large to sequester the desired component from at least 90% of the formulation in the bottle.

The present disclosure provides salts of any one or both of a therapeutic agent and a preservative. Pharmaceutically-acceptable salts include, for example, acid-addition salts and base-addition salts. The acid that is added to the compound to form an acid-addition salt can be an organic acid or an inorganic acid. A base that is added to the compound to form a base-addition salt can be an organic base or an inorganic base. In some embodiments, a pharmaceutically-acceptable salt is a metal salt.

Metal salts can arise from the addition of an inorganic base to a compound of the present disclosure. The inorganic base consists of a metal cation paired with a basic counterion, such as, for example, hydroxide, carbonate, bicarbonate, or phosphate. The metal can be an alkali metal, alkaline earth metal, transition metal, or main group metal. In some embodiments, the metal is lithium, sodium, potassium, cesium, cerium, magnesium, manganese, iron, calcium, strontium, cobalt, titanium, aluminum, copper, cadmium, or zinc.

In some embodiments, a metal salt is a lithium salt, a sodium salt, a potassium salt, a cesium salt, a cerium salt, a magnesium salt, a manganese salt, an iron salt, a calcium salt, a strontium salt, a cobalt salt, a titanium salt, an aluminum salt, a copper salt, a cadmium salt, or a zinc salt.

Acid addition salts can arise from the addition of an acid to a compound of the present disclosure. In some embodiments, the acid is organic. In some embodiments, the acid is inorganic. In some embodiments, the acid is hydrochloric acid, hydrobromic acid, hydroiodic acid, nitric acid, nitrous acid, sulfuric acid, sulfurous acid, a phosphoric acid, isonicotinic acid, lactic acid, salicylic acid, tartaric acid, ascorbic acid, gentisinic acid, gluconic acid, glucuronic acid, saccharic acid, formic acid, benzoic acid, glutamic acid, pantothenic acid, acetic acid, propionic acid, butyric acid, fumaric acid, succinic acid, methanesulfonic acid, ethanesulfonic acid, benzenesulfonic acid, p-toluenesulfonic acid, citric acid, oxalic acid, or maleic acid.

In some embodiments, the salt is a hydrochloride salt, a hydrobromide salt, a hydroiodide salt, a nitrate salt, a nitrite salt, a sulfate salt, a sulfite salt, a phosphate salt, isonicotinate salt, a lactate salt, a salicylate salt, a tartrate salt, an ascorbate salt, a gentisinate salt, a gluconate salt, a glucuronate salt, a saccharate salt, a formate salt, a benzoate salt, a glutamate salt, a pantothenate salt, an acetate salt, a propionate salt, a butyrate salt, a fumarate salt, a succinate salt, a methanesulfonate (mesylate) salt, an ethanesulfonate salt, a benzenesulfonate salt, a p-toluenesulfonate salt, a citrate salt, an oxalate salt, or a maleate salt.

Solution, Emulsion, or Suspension

Provided herein are solutions, emulsions, or suspensions of a therapeutic agent and a preservative. In some embodiments, provided herein are compositions comprising a therapeutically effective amount of any compound or salt of any one of the preservatives and/or therapeutic agents of the present disclosure. In some embodiments, a therapeutic solution, emulsion, or suspension may be used in any of the methods described herein. The solution, emulsion, or suspension may additionally comprise one or more pharmaceutically acceptable excipients.

In some embodiments, a compound of preservative and/or therapeutic agent may be used for the treatment of a therapeutic disorder such as, dry eye, bacterial infection, glaucoma, hypertension, inflammation, allergic conjunctivitis, hypotrichosis of the eyelashes, fungal infection, etc. Additionally or alternatively, a compound of a preservative and/or therapeutic agent may be used during a preventative, diagnostic, or therapeutic ophthalmological procedure, for example, local anesthetic, pupil dilation, etc. A formulation administered to the eye may be administered topically, for example, with an eye drop.

A compound of the therapeutic agent described herein can be present in a solution, emulsion, or suspension of the present disclosure at a concentration of, for example, about 500 nM, about 600 nM, about 700 nM, about 800 nM, about 900 nM, about 1 µM, about 2 µM, about 3 µM, about 4 µM, about 5 µM, about 6 µM, about 7 µM, about 8 µM, about 9 µM, about 10 µM, about 20 µM, about 30 µM, about 40 µM, about 50 µM, about 60 µM, about 70 µM, about 80 µM, about 90 µM, about 100 µM, about 150 µM, about 200 µM, about 250 µM, about 300 µM, about 350 µM, about 400 µM, about 450 µM, about 500 µM, about 550 µM, about 600 µM, about 650 µM, about 700 µM, about 750 µM, about 800 µM, about 850 µM, about 900 µM, about 1 mM, about 5 mM, about 10 mM, about 15 mM, about 20 mM, about 25 mM, about 30 mM, about 35 mM, about 40 mM, about 45 mM, about 50 mM, about 55 mM, about 60 mM, about 65 mM, about 70 mM, about 75 mM, about 80 mM, about 85 mM, about 90 mM, about 95 mM, or about 100 mM. The compound of a therapeutic agent described herein may be present in a solution, emulsion, or suspension within a range of concentrations, the range being defined by an upper and lower value selected from any of the preceding concentrations. For example, the compound or salt of a therapeutic agent of the disclosure may be present in the solution, emulsion, or suspension at a concentration of from about 1 nM to about 100 mM, about 10 nM to about 10 mM, about 100 nM to about 1 mM, about 500 nM to about 1 mM, about 1 mM to about 50 mM, about 10 mM to about 40 mM, about 20 mM to about 35 mM, or about 20 mM to about 30 mM.

In some embodiments, a solution, emulsion, or suspension such as an aqueous solution of the disclosure, comprises from about 0.001 wt % to about 0.3 wt % of the compound of any one of the preservatives disclosed herein. In some embodiments, a solution, emulsion, or suspension such as an aqueous solution of the disclosure, comprises about 0.001 wt %, about 0.002 wt %, about 0.003 wt %, about 0.004 wt %, about 0.005 wt %, about 0.006 wt %, about 0.007 wt %, about 0.008 wt %, about 0.009 wt %, about 0.01 wt %, about 0.02 wt %, about 0.03 wt %, about 0.04 wt %, about 0.05 wt %, about 0.06 wt %, about 0.07 wt %, about 0.08 wt %, about 0.09 wt %, about 0.1 wt %, about 0.2 wt %, about 0.3 wt %, about 0.4 wt %, about 0.5 wt %, about 0.6 wt %, about 0.7 wt %, about 0.8 wt %, about 0.9 wt %, about 1 wt %, about 1.1 wt %, about 1.2 wt %, about 1.3 wt %, about 1.4 wt %, about 1.5 wt %, about 1.6 wt %, about 1.7 wt %, about 1.8 wt %, about 1.9 wt %, about 2 wt %, about 3 wt %, about 4 wt %, about 5 wt %, about 6 wt %, about 7 wt %, about 8 wt %, about 9 wt %, or about 10 wt % of a compound of the preservative described herein.

The preservative described herein can be present in a solution, emulsion, or suspension of the present disclosure at a concentration of, for example, about 500 nM, about 600 nM, about 700 nM, about 800 nM, about 900 nM, about 1 µM, about 2 µM, about 3 µM, about 4 µM, about 5 µM, about 6 µM, about 7 µM, about 8 µM, about 9 µM, about 10 µM, about 20 µM, about 30 µM, about 40 µM, about 50 µM, about 60 µM, about 70 µM, about 80 µM, about 90 µM, about 100 µM, about 150 µM, about 200 µM, about 250 µM, about 300 µM, about 350 µM, about 400 µM, about 450 µM, about 500 µM, about 550 µM, about 600 µM, about 650 µM, about 700 µM, about 750 µM, about 800 µM, about 850 µM, about 900 µM, about 1 mM, about 5 mM, about 10 mM, about 15 mM, about 20 mM, about 25 mM, about 30 mM, about 35 mM, about 40 mM, about 45 mM, about 50 mM, about 55 mM, about 60 mM, about 65 mM, about 70 mM, about 75 mM, about 80 mM, about 85 mM, about 90 mM, about 95 mM, or about 100 mM. The compound of a preservative described herein may be present in a composition within a range of concentrations, the range being defined by an upper and lower value selected from any of the preceding concentrations. For example, the compound of a preservative of the disclosure may be present in the solution, emulsion, or suspension at a concentration of from about 1 nM to about 100 mM, about 10 nM to about 10 mM, about 100 nM to about 1 mM, about 500 nM to about 1 mM, about 1 mM to about 50 mM, about 10 mM to about 40 mM, about 20 mM to about 35 mM, or about 20 mM to about 30 mM.

Solutions, emulsions, or suspensions of the disclosure can be formulated at any suitable pH. In some embodiments, the pH of the solution emulsion or suspension is about 4, about 4.05, about 4.1, about 4.15, about 4.2, about 4.25, about 4.3, about 4.35, about 4.4, about 4.45, about 4.5, about 4.55, about 4.6, about 4.65, about 4.7, about 4.75, about 4.8, about 4.85, about 4.9, about 4.95, about 5, about 5.1, about 5.2, about 5.3, about 5.4, about 5.5, about 5.6, about 5.7, about 5.8, about 5.9, about 6, about 6.1, about 6.2, about 6.3, about 6.4, about 6.5, about 6.6, about 6.7, about 6.8, about 6.9, about 7, about 7.1, about 7.2, about 7.3, about 7.4, about 7.5, about 7.6, about 7.7, about 7.8, about 7.9, about 8, about 8.1, about 8.2, about 8.3, about 8.4, about 8.5, about 8.6, about 8.7, about 8.8, about 8.9, or about 9 pH units. In some embodiments, the pH of the solution, emulsion, or suspension is from about 4 to about 10, about 5 to about 9, about 6 to about 8, about 6.5 to about 8, about 7 to about 8, about 7.2 to about 8, about 7.2 to about 7.8, about 7.3 to about 7.5, or about 7.35 to about 7.45. In some embodiments the pH of the solution, emulsion, or suspension is about 7.4.

In some embodiments, solutions, emulsions, or suspensions of the present disclosure further comprise one or more physiologically acceptable carriers including excipients and auxiliaries which facilitate processing of the pharmaceutical agent into preparations which are used pharmaceutically. Proper formulation is dependent upon the route of administration chosen.

In some embodiments, the addition of an excipient to a pharmaceutical formulation of the present disclosure can increase or decrease the viscosity of the composition by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%. In some embodiments, the addition of an excipient to a pharmaceutical formulation of the present disclosure can increase or decrease the viscosity of the composition by no greater than 5%, no greater than 10%, no greater than 15%, no greater than 20%, no greater than 25%, no greater than 30%, no greater than 35%, no greater than 40%, no greater than 45%, no greater than 50%, no greater than 55%, no greater than 60%, no greater than 65%, no greater than 70%, no greater than 75%, no greater than 80%, no greater than 85%, no greater than 90%, no greater than 95%, or no greater than 99%. Examples of ranges which the viscosity change falls within can be created by combining any two of the preceding percentages. For example, the addition of an excipient can increase or decrease the viscosity of the composition by 5% to 99%, by 10% to 95%, by 20% to 70% or by 35% to 55%.

In some embodiments, solutions, emulsions, or suspensions of the present disclosure further comprise an agent for adjusting the osmolarity of the solution, emulsion, or suspension, e.g., mannitol, sodium chloride, sodium sulfate, dextrose, potassium chloride, glycerin, propylene glycol, calcium chloride, and magnesium chloride. In some embodiments, the solution, emulsion, or suspension comprises from about 0.1 wt % to about 10 wt %, about 0.5 wt % to about 8 wt %, about 1 wt % to about 5 wt %, about 1 wt % to about 4 wt %, or about 1 wt % to about 3 wt % of an agent for adjusting the osmolarity of the solution, emulsion, or suspension. In some embodiments, the solution, emulsion, or suspension of the disclosure has an osmolarity from about 10 mOsm to about 1000 mOsm, about 100 mOsm to about 700 mOsm, about 200 mOsm to about 400 mOsm, about 250 mOsm to about 350 mOsm or even about 290 mOsm to about 310 mOsm.

The amount of the excipient in a solution, emulsion, or suspension of the present disclosure can be about 0.01%, about 0.02%, about 0.03%, about 0.04%, about 0.05%, about 0.06%, about 0.07%, about 0.08%, about 0.09%, about 0.1%, about 0.2%, about 0.3%, about 0.4%, about 0.5%, about 0.6%, about 0.7%, about 0.8%, about 0.9%, about 1%, about 1.5%, about 2%, about 2.5%, about 3%, about 3.5%, about 4%, about 4.5%, about 5%, about 6%, about 7%, about 8%, about 9%, about 10%, about 15%, about 20%, about 25%, about 30%, about 35%, about 40%, about 45%, about 50%, about 55% about 60%, about 65%, about 70%, about 75%, about 80%, about 85%, about 90%, about 95%, about 99%, or about 100% by mass or by volume of the unit dosage form. The amount of the excipient in a solution, emulsion, or suspension can be between 0.01% and 1000%, between 0.02% and 500%, between 0.1% and 100%, between 1% and 50%, between 0.01% and 1%, between 1% and 10%, between 10% and 100%, between 50% and 150%, between 100% and 500%, or between 500% and 1000% by mass or by volume of the unit dosage form.

The ratio of a compound of a therapeutic agent of the present disclosure to an excipient in a pharmaceutical formulation of the present disclosure can be about 100:about 1, about 95:about 1, about 90:about 1, about 85:about 1, about 80:about 1, about 75:about 1, about 70:about 1, about 65:about 1, about 60:about 1, about 55:about 1, about 50:about 1, about 45:about 1, about 40:about 1, about 35:about 1 about 30:about 1, about 25:about 1, about 20:about 1, about 15:about 1, about 10:about 1, about 9:about 1, about 8:about 1, about 7:about 1, about 6:about 1, about 5:about 1, about 4:about 1, about 3:about 1, about 2:about 1, about 1:about 1, about 1:about 2, about 1:about 3, about 1:about 4, about 1:about 5, about 1:about 6, about 1:about 7, about 1:about 8, about 1:about 9, or about 1:about 10. The ratio of a compound of a therapeutic agent to an excipient in a solution, emulsion, or suspension of the present disclosure can be within the range of between about 100:about 1 and about 1 to about 10, between about 10:about 1 and about 1:about 1, between about 5:about 1 and about 2:about 1.

Pharmaceutically acceptable carriers are well known in the art and include, for example, aqueous solutions such as water or physiologically buffered saline or other solvents or vehicles such as glycols, glycerol, oils such as olive oil, or organic esters. The excipients can be chosen, for example, to effect delayed release of an agent or to selectively target one or more cells, tissues or organs. The composition can also be present in a solution suitable for topical administration, such as an eye drop.

In some embodiments, the solution emulsion or suspension provided herein comprises an alcohol as an excipient. Non-limiting examples of alcohols include ethanol, propylene glycol, glycerol, polyethylene glycol, chlorobutanol, isopropanol, xylitol, sorbitol, maltitol, erythritol, threitol, arabitol, ribitol, mannitol, galactilol, fucitol, lactitol, and combinations thereof.

Methods for the preparation of compositions comprising the compounds described herein can include formulating the compounds with one or more inert, pharmaceutically-acceptable excipients. Liquid compositions include, for example, solutions in which a compound is dissolved, emulsions comprising a compound, or a solution containing liposomes, micelles, or nanoparticles comprising a compound as disclosed herein. These compositions can also contain minor amounts of nontoxic, auxiliary substances, such as wetting or emulsifying agents, pH buffering agents, and other pharmaceutically-acceptable additives.

Examples

Hydrophilic Drugs
Calculating the Partition Coefficient of API and BAK in the Particle Matrix The partition coefficients of hydrophilic drugs and BAK in OxPO particles are obtained by drug uptake studies. The mass of drug or BAK partitioned into OxPO matrix is determined by monitoring the amount of drug or BAK lost in the concentrated aqueous drug/PBS or BAK/PBS loading solutions. The amount of drug loss from the concentrated aqueous phase was quantified by time-dependent measurements using reverse phase UPLC analysis.

The partition coefficient of drug or BAK solution in the particle matrix is given by $$k = \frac{C_{p,f}}{C_{w,f}} = \frac{V_w(C_{w,f} - C_{w,i})}{V_p C_{w,f}}, \qquad \text{(Equation 1)}$$

where $V_w$ and $V_p$ are volumes of drug-PBS/BAK-PBS aqueous solution and volume of the particle matrix respectively, $C_{p,f}$ and $C_{w,f}$ denote the drug or BAK concentration in the particle matrix and aqueous phase at equilibrium, and $C_{w,i}$ represents the initial concentration of the drug or BAK loading solution.

A more accurate estimate BAK diffusivity is obtained by fitting the experimental BAK uptake data to a transient diffusion model under non-perfect sink conditions. The transport of solute through these OxPO materials occurred through swelling of the polymer, bulk and surface diffusion. To maintain the model's simplicity, we assumed preservative diffusion through the filter material to be purely Fickian.

Assuming the BAK diffusivity, $D_g$ and partition coefficient K are independent of concentration of BAK, transport in the radial direction can be described as:

$$\frac{\partial C_g}{\partial t} = D_g \left( \frac{\partial^2 C_g}{\partial r^2} + \frac{2}{r} \frac{\partial C_g}{\partial r} \right), \quad \text{(Equation 2)}$$

where $C_g$ is the BAK concentration in the OxPO particle matrix. The boundary and initial conditions for diffusion in the particle matrix are $$\frac{\partial C_g}{\partial y_2}(y_2 = 0) = 0 \quad \text{(Equation 3)}$$

$$C(y_2 = h_g) = K C_f(t) \quad \text{(Equation 4)}$$

$$C_g(t = 0) = 0 \quad \text{(Equation 5)}$$

The boundary condition (Equation 3) arises from symmetry of the particle matrix and that in (Equation 4) assumes equilibrium between concentration of the preservative in the polymer matrix and the surrounding formulation present in the aqueous BAK solution in the vial. A mass balance on the aqueous BAK reservoir in the scintillation vial yields the following equation:

$$V_w \frac{dC_w}{dt} = -D_g A_g n_d \frac{\partial C_g}{\partial r}(r = R) \quad \text{(Equation 6)}$$

$$V_w \frac{dC_w}{dt} = -D_g \frac{3V_g}{R} \frac{\partial C_g}{\partial r}(r = R), \quad \text{(Equation 7)}$$

where $V_w$ is the volume of BAK/PBS solution in the aqueous reservoir whose concentration is 1 mg/mL. The modelled diffusion equation is solved using finite difference schemes in MATLAB with BAK diffusivity and partition coefficient determined by curve fitting experimental BAK uptake data for different OxPO compositions to the model and optimization through fminsearch module.

The partition coefficients of hydrophilic drugs and BAK in OxPO particles is determined by reverse phase UPLC analysis.

Oxidized Low Density Polyethylene (OxLDPE) and Oxidized High Density Polyethylene (OxHDPE) are commercially available from Honeywell (e.g. A-C 395) and DEUREX (e.g. DEUREX EO 45). Oxidized Fischer-Tropsch Wax (OxFTW) is available from DEUREX (e.g. DEUREX TO-84). Several different grades of these OxPOs are available; they are typically characterized by their molecular weight, drop point (melting point), density, hardness, particle size and acid number (mg KOH/g).

BAK (pharma grade) was obtained from Sigma-Aldrich (St. Lewis, Mo.); it was a mixture of approximately 70% C12 and 30% C14 Benzylalkyldimethylammonium Chloride. Research grade Timolol Maleate and Brimonidine Tartrate were obtained from BOC Sciences (Shirley, N.Y.). Phosphate Buffered Saline (PBS) was obtained from Fisher Scientific. Hydroxyethyl Cellulose (Natrosol 250H) was obtained from Ashland Chemical. Mannitol was obtained from JT Baker Co.

Washing Procedure for OxPOs

Approximately 70 g of OxHDPE (Honeywell's A-C 395A; sieved fraction at 63-125 um) was added to a 2 L beaker on a stirrer hotplate containing 1 L of 0.1 N aq. acetic acid. The mixture was heated with stirring for 1 h at 65-70° C. The product was collected on a 63 μm sieve and thoroughly washed with about 3 L of DI water. The washed OxHDPE was dried in a vacuum oven at ambient temperature to yield about 65 g of white powder. The BAK partition coefficient of this powder was determined to be 360. Other OxPOs were washed in a similar manner. The wash solution was either neutral water, 0.1 N aq. acetic acid or 0.1 N aq. ammonium hydroxide.

Ultra Performance Liquid Chromatography (UPLC):

The UPLC system consisted of a Waters Aquity UPLC (Waters, Milford, Mass., US) equipped with a Binary pump, online degasser, column heater, autosampler and UV/Vis detector. Data collection and analysis were performed using Empower 3 FR 4 (Waters). Separation was achieved on a Waters UPLC, HSS C18 1.8 μm, 3.0 mm×100 mm column protected using a Waters HSS C18 1.8 um, VanGuard Pre-Column.

For the APIs Timolol and Brimonidine, the flow rate was 1.0 ml/min, solvent A was acetonitrile and solvent B was 0.1% Trifluoroacetic Acid. For the first 0.40 min, the solvent was 10% A/90% B; the next 1.4 min the gradient ramped to 100% A; held at 100% A for 2.2 min; switched back to 10% A/90% B. Total run time 3.5 min. The results for UPLC were recorded on UV-Vis ($\lambda$=256 nm and 297 nm) detectors.

For BAK, the flow rate was 0.75 ml/min, solvent A was acetonitrile and solvent B was 0.03N HCl. For the first 1.0 min, the solvent was 60% A/40% B; the next 3.5 min the gradient ramped to 90% A/10% B; held at 90% A/10% B for 0.5 min.; the next 0.2 min the gradient ramped to 20% A/80% B; then switched back to 60% A/40% B. Total run time 7.0 min. The results for UPLC were recorded on UV-Vis ($\lambda$=210 nm) detectors.

Prior to analysis of target drugs and BAK, standards were made to determine the UV absorbances. A 3D spectrum was collected and the optimal UV wavelength was selected. Based on the area counts the target sample was then diluted within the linear range. To determine the linear range a series of standards were made and then plotted onto a graph, the graph was then fitted with a linear trendline. The trendline was set to go through the 0 intercept and if the linear fit was above 0.9900 the dilution was determined to be adequate.

Procedure for Determining the BAK Partition Coefficient

To a 20 ml scintillation vial was added 0.2 g of the OxPO being tested and 5.0 ml of a 1000 ppm BAK solution in normal PBS. The vial was capped and swirled on a rotary shaker for 2 days. The supernatant solution was filtered through a 0.45 micron filter to remove any solids. A portion of the filtrate was diluted 1:1 with acetonitrile and analyzed by UPLC as described above.

Procedure for Determining the API Partition Coefficient

To a 20 ml scintillation vial was added 0.1 g of the OxPO being tested and 5.0 ml of an API formulation. The vial was capped and swirled on a rotary shaker for 2 days. The supernatant solution was filtered through a 0.45 micron filter to remove any solids. A portion of the filtrate was diluted 100:1 with 50% aq. acetonitrile and analyzed by UPLC as described above. A portion of the original API solution was filtered, diluted and analyzed by UPLC as a comparative standard.

Procedure for Determining the BAK Partition Coefficient

To a 20 ml scintillation vial was added 0.2 g of the OxPO being tested and 5.0 ml of a 1000 ppm BAK solution in normal PBS. The vial was capped and swirled on a rotary shaker for 48 hrs. The supernatant solution was filtered through a 0.45 μm filter to remove any solids. A portion of the filtrate was diluted 1:1 with acetonitrile and analyzed by UPLC as described above. To calculate the ratio of the BAK adsorbed on the OxPO to the BAK remaining in the solution, the following formula was used (PC=partition coefficient):

PC=[(initial BAK conc.−final BAK conc.)×wt. of solution]/wt. of OxPO×final BAK conc.

For example, if the initial BAK concentration was 1000 ppm, the final BAK concentration was 14 ppm, using 5.0 g of solution and 0.20 g of OxPO powder, the PC=1761. In this test PC values >50 are desired; values >100 are preferred and values >1000 demonstrated nearly complete adsorption of BAK.

Summary of BAK Partition Coefficients for OxPOs

The partition coefficient test described above was used to determine the values for OxPOs that were classified to various particle sizes, washed with neutral, acidic or basic solutions and dried.

| material | source | Acid No. | Particle size (μm) | Wash solution | BAK Part. coefficient | Type of polymer |
|---|---|---|---|---|---|---|
| A-C 395 | Honeywell | 40 | 125-250 | unwashed | 54 | OxHDPE |
| A-C 395 | Honeywell | 40 | 125-250 | neutral | 1100 | OxHDPE |
| A-C 395 | Honeywell | 40 | 63-125 | 0.1N AcOH | 1813 | OxHDPE |
| A-C 395 | Honeywell | 40 | 63-125 | 0.1N NH$_4$OH | 113 | OxHDPE |
| A-C 330 | Honeywell | 30 | mixture | neutral | 59 | OxHDPE |
| EO 45K | Deurex | 25 | 125-500 | neutral | 71 | OxHDPE |
| EO 45K | Deurex | 25 | 125-500 | 0.1N AcOH | 81 | OxHDPE |
| TO 84 | Deurex | 30-40 | 125-250 | unwashed | 2,475 | OxFTW |
| TO 84 | Deurex | 30-40 | 125-250 | 0.1N AcOH | 11,880 | OxFTW |
| LDPE #A10239 | Alfa Aesar | 0 | 500 | unwashed | 0 | LDPE |
| LDPE #A10239 | Alfa Aesar | 0 | 500 | 0.1N AcOH | 0.2 | LDPE |

Preparation of Combination Timolol Maleate and Dorzolamide Hydrochloride Ophthalmic Solution To 60.0 g of ultrapure water was added 0.090 g hydroxyethyl cellulose (Natrosol 250H) and the solution was stirred overnight to dissolve. Subsequently, 0.176 g sodium citrate dihydrate and 0.960 g mannitol were added and the mixture was stirred until completely dissolved. 1.37 g Dorzolamide Hydrochloride, 0.420 g Timolol Maleate and 0.045 g of a 10% aqueous solution of BAK were added and incorporated. The pH was adjusted to 5.65 with 0.01N NaOH solution. The final nominal concentrations are reported below.

| Component | Conc. % (w/v) | API conc. |
|---|---|---|
| Timolol Maleate (0.5% free base) | 0.683 | 5.00 mg/ml |
| Dorzolamide Hydrochloride (2.0% free base) | 2.26 | 20.0 mg/ml |
| BAK (70/30 C12/C14) | 0.0075 | 75 μg/ml |
| Sodium Citrate dihydrate | 0.2941 | |
| Mannitol | 1.6 | |

Procedure for Packing Dropper Tips with OxPO

An empty dropper tip equipped with a 25 μm filter at the tip exit was packed with approximately 0.40-0.45 mg of OxPO and the backing filter was attached to retain the OxPO packing in place. The weight of the OxPO packing was recorded. The packed tip was then inserted into the neck of an 8 ml dropper bottle containing 5 ml of the API/BAK test solution.

30 Day Drop Test for Combination Timolol/Brimonidine/BAK Formulation 5 ml of the formulation described above containing nominally 5.0 mg/ml Timolol, 20.0 mg/ml Dorzolamide and 75 μg/ml BAK was loaded into six eyedropper bottles packed with OxHDPE (A-C 395, 125-250 μm, acid washed) as described above. Drops were obtained from each bottle twice a day (AM and PM 8 hours apart) and analyzed by HPLC for API and BAK. The results are summarized in the table below. This experiment demonstrated the ability of the OxPO to remove >95% of the BAK and retain >95% of the API over the 30-day test period.

| 30-day Drop Test Summary | | | |
|---|---|---|---|
| Day | BAK | Timolol | Dorzolamide |
| Initial | 75 (μg/ml) | 5.04 (mg/ml) | 21.0 (mg/ml) |
| 1A | 0.088 | 4.93 | 20.0 |
| 1P | ND | 4.91 | 20.1 |
| 2A | ND | 4.51 | 19.2 |
| 2P | ND | 4.64 | 19.4 |
| 3A | ND | 4.60 | 19.5 |
| 3P | ND | 4.65 | 19.6 |
| 4A | ND | 4.59 | 19.3 |
| 4P | ND | 4.72 | 19.7 |
| 5A | ND | 4.68 | 19.7 |
| 5P | ND | 4.78 | 19.8 |
| 6A | ND | 4.76 | 19.8 |
| 6P | ND | 4.90 | 20.2 |
| 7A | ND | 4.86 | 20.3 |
| 7P | ND | 4.91 | 20.3 |
| 8A | ND | 4.85 | 20.1 |
| 8P | ND | 4.89 | 20.2 |
| 9A | ND | 4.84 | 19.8 |
| 9P | ND | 4.87 | 19.5 |
| 10A | ND | 4.89 | 19.8 |
| 10P | ND | 4.90 | 20.1 |
| 11A | ND | 4.89 | 19.9 |
| 11P | ND | 4.96 | 19.9 |
| 12A | ND | 4.86 | 19.8 |
| 12P | ND | 4.95 | 19.9 |
| 13A | ND | 4.89 | 19.9 |
| 13P | ND | 4.93 | 19.9 |
| 14A | ND | 4.86 | 19.7 |
| 14P | ND | 4.97 | 20.0 |
| 15A | ND | 4.87 | 19.8 |
| 15P | ND | 4.93 | 19.9 |
| 16A | ND | 4.90 | 19.5 |
| 16P | ND | 5.01 | 19.8 |
| 17A | ND | 4.90 | 19.4 |
| 17P | ND | 4.97 | 19.4 |
| 18A | ND | 4.98 | 19.7 |
| 18P | ND | 4.97 | 19.6 |
| 19A | ND | 4.87 | 19.2 |
| 19P | ND | 4.98 | 19.5 |
| 20A | ND | 4.99 | 19.6 |
| 20P | ND | 5.02 | 19.7 |
| 21A | ND | 4.92 | 19.6 |
| 21P | ND | 4.95 | 19.7 |
| 22A | ND | 4.98 | 20.0 |
| 22P | ND | 4.93 | 19.5 |
| 23A | ND | 4.96 | 19.8 |
| 23P | ND | 4.97 | 19.8 |
| 24A | ND | 4.94 | 19.8 |
| 24P | ND | 4.96 | 19.8 |
| 25A | ND | 4.90 | 19.6 |
| 25P | ND | 4.93 | 19.7 |
| 26A | ND | 4.97 | 20.2 |
| 26P | ND | 4.96 | 20.1 |
| 27A | ND | 4.96 | 20.1 |
| 27P | ND | 4.97 | 20.1 |
| 28A | ND | 4.93 | 20.1 |
| 28P | ND | 4.95 | 19.9 |

-continued

30-day Drop Test Summary

| Day | BAK | Timolol | Dorzolamide |
|---|---|---|---|
| 29A | ND | 4.90 | 19.6 |
| 29P | ND | 4.93 | 19.6 |
| 30A | ND | 4.98 | 20.1 |
| 30P | ND | 4.97 | 20.1 |

A = 1st set of day
P = 2nd set of day
ND = None Detected

Illustrative solutions, emulsions, or suspensions which can be used in aspects of the pharmaceutical formulation disclosed herein are shown in Tables 1 to 4. Example solutions, emulsions, or suspensions in the tables above may be integrated into preservative removing devices and methods of removing a preservative of the present disclosure. One or more embodiments, variations, and examples of the preservative removing devices, matrices, and methods described herein may be incorporated into an eye drop dispensing system, which system may comprise a squeezable bottle. A squeezable bottle may comprise a reservoir in which a fluid may be stored. A fluid stored in the reservoir may comprise an embodiment, variation, or example of solutions, emulsions, or suspensions described herein, including those examples provided in Tables 1 to 4.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the disclosure described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A particulate plug for removing a preservative from a solution, suspension, or emulsion comprising a drug, the particulate plug comprising microparticles of a polymer comprising oxidized polyolefin (OxPO) wherein the microparticles form a particulate plug having a hydraulic permeability greater than 0.01 Da, wherein the particulate plug formed from the microparticles of the polymer comprising the OxPO has a partition coefficient for the preservative that is greater than a partition coefficient for the drug.

2. The particulate plug of claim 1, wherein the oxidized polyolefin (OxPO) is selected from a homopolymer or copolymer of ethylene, propylene, 1-butene, 4-methyl-1-pentene, 3-methyl-1-butene, 4,4-dimethyl-1-pentene, 3-methyl-1-pentene, 4-methyl-1-hexene, 5-ethyl-1-hexene, 6-methyl-1-heptene, 1-hexene, 1-heptene, 1-octene, 1-nonene, or 1-decene.

3. The particulate plug of claim 1, wherein the oxidized polyolefin (OxPO) is a homopolymer or a copolymer of oxidized high density polyethylene (OxHDPE).

4. The particulate plug of claim 1, wherein the oxidized polyolefin (OxPO) is a polymer formed by the Fischer-Tropsch process.

5. The particulate plug of claim 1, wherein the drug is selected from timolol maleate, levofloxacin, dorzolamide, brimonidine tartrate, or a combination thereof.

6. The particulate plug of claim 1, wherein the preservative comprises:
benzalkonium chloride (BAK);
a quaternary ammonium compound;
a solution of borate, sorbitol, propylene glycol, and zinc; or
stabilized oxychloro complexes.

7. The particulate plug of claim 1, wherein the particulate plug comprises a packed bed of particles.

8. The particulate plug of claim 1, wherein the particulate plug is sintered to fuse the particulate plug as a porous monolith.

9. The particulate plug of claim 1, wherein the particulate plug is pre-equilibrated with the solution, suspension, or emulsion.

10. The particulate plug of claim 1, wherein the OxPO comprises an acid value of about 41 mg KOH/g.

11. The particulate plug of claim 1, wherein the OxPO comprises a drop point between 125 and 135 Celsius.

12. The particulate plug of claim 1, wherein the OxPO comprises a density of about 0.98 grams per cubic centimeter.

13. The particulate plug of claim 1, wherein the OxPO comprises a viscosity of 4.00 mPas at 190 Celsius.

14. The particulate plug of claim 1, wherein the microparticles of the polymer comprising OxPO are sized between 125 and 250 microns.

15. The particulate plug of claim 1, wherein the drug comprises a hydrophilic drug.

16. The particulate plug of claim 1, wherein the OxPO comprises an acid value of at least 20 mg KOH/g.

17. The particulate plug of claim 16, wherein the OxPO comprises an acid value of at least 30 mg KOH/g.

18. A method of removing a preservative from a drug solution, suspension, or emulsion, comprising:
providing a container having an extended outlet and a chamber for holding the drug solution, suspension, or emulsion comprising at least one drug and a preservative, the container comprising a particulate plug within the extended outlet, wherein the particulate plug comprises microparticles of a polymer comprising oxidized polyolefin (OxPO), and wherein the microparticles form a particulate plug having a hydraulic permeability greater than 0.01 Da; and
forcing the drug solution, suspension, or emulsion through the particulate plug, wherein the particulate plug selectively removes a preservative from the solution, emulsion, or suspension.

19. The method of claim 18, wherein the particulate plug has a partition coefficient for the preservative that is greater than a partition coefficient for the at least one drug.

20. The method of claim 18, wherein the particulate plug has a partition coefficient for the preservative that is at least 100 and a partition coefficient for the at least one drug that is less than 1.

21. The method of claim 18, wherein the container is an eye drop bottle comprising a holder assembly configured to retain the particulate plug.

22. The method of claim 21, wherein the holder assembly comprises a formulation entry face and a formulation exit face and wherein the formulation entry face and the formulation exit face comprise filters.

23. The method of claim 21, wherein the holder assembly comprises a solution, suspension, or emulsion permeable bag around the particulate plug.

* * * * *